US007544685B2

(12) United States Patent
Bang-Andersen et al.

(10) Patent No.: US 7,544,685 B2
(45) Date of Patent: Jun. 9, 2009

(54) 2,3-DIHYDROINDOLE COMPOUNDS

(75) Inventors: Benny Bang-Andersen, Copenhagen S (DK); Krestian Larsen, Ringsted (DK); Niels Mørk, Virum (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 131 days.

(21) Appl. No.: 11/504,186

(22) Filed: Aug. 15, 2006

(65) Prior Publication Data

US 2007/0043058 A1     Feb. 22, 2007

Related U.S. Application Data

(60) Provisional application No. 60/709,174, filed on Aug. 17, 2005.

(51) Int. Cl.
*A61K 31/496* (2006.01)
*A61K 31/437* (2006.01)
*C07D 209/14* (2006.01)
*C07D 487/04* (2006.01)
*A61K 31/454* (2006.01)
*A61K 31/4439* (2006.01)
*C07D 401/0411* (2006.01)

(52) U.S. Cl. ............... 514/253.04; 514/254.09; 514/323; 514/339; 544/362; 544/373; 546/201; 546/278.1

(58) Field of Classification Search ............ None
See application file for complete search history.

(56) References Cited

U.S. PATENT DOCUMENTS 5,700,802 A    12/1997  Curtis et al.
6,313,297 B1   11/2001  Herwig et al.

FOREIGN PATENT DOCUMENTS

| EP | 0 624 584 B1 | 8/1998 |
| WO | WO 94/20497 A1 | 9/1994 |
| WO | WO 94/22839 A1 | 10/1994 |
| WO | 98/28293 * | 7/1998 |
| WO | WO 98/28293 A | 7/1998 |
| WO | WO 99/36412 A2 | 7/1999 |
| WO | WO 99/37304 A1 | 7/1999 |

OTHER PUBLICATIONS

Jones et al. Pharmacology, Biochemistry and Behavior, vol. 71,p. 555-568 (2002).*
Robichaud et al. in Annual Reports in Medicinal Chemistry, vol. 36, p. 11-20 (2000).*
Truffinet et al. Am.J.Psychiatry, vol. 156, p. 419-425 (1999).*
Arora et al. Bioorganic & Medicinal Chemistry Letters, vol. 15, p. 5253-5256 (2005).*
Mansbach, R.S., et al., "Selective dopamine D4 receptor antagonists reverse apomorphine-induced blockade or prepulse inhibition", Psychopharmacology, 1998, 194-200, vol. 135.
McCracken, JT, et al., "Evidence for linkage of a tandem duplication polymorphism upstream of the dopamine D4 receptor gene (DRD4) with attention deficit hyperactivity disorder (ADHD)", Molecular Psychiatry, 2000, 531-536, vol. 5.
Meert, T.F. and Janssen, P.A.J., "Psychopharmacology of Ritanserin: Comparison With Chlordiazepoxide", Drug Dev. Res., 1989, 119-144, vol. 18.
Obach, R.S., et al., "The Prediction of Human Pharmacokinetic Parameters from Preclinical and In Vitro Metabolism Data", JPET, 1997, 46-58, vol. 283, No. 1.
Sanner, M. A., "Selective dopamine D4 receptor antagonists", Exp. Opin. Ther. Patents, 1998, 383-393, vol. 8, No. 4.
Van Tol H.H.M., et al., "Cloning of the gene for a human dopamine D4 receptor with high affinity for the antipsychotic clozapine", Nature, Apr. 18, 1991, 610-614, vol. 350.
Zhang, K., et al., "Effects of dopamine D4 receptor-selective antagonists on motor hyperactivity in rats with neonatal 6-hydroxydopamine lesions", Psychopharmacology, 2002, 100-106, vol. 161.
Benet, L.Z., "The Role of Pharmacokinetics in the Drug Development Process", Integration of Pharmacokinetics, Pharmacodynamics, and Toxicokinetics in Rational Drug Development, Edited by A. Yacobi, et al., 1993, pp. 115-123, Plenum Press, New York.
Carlsson, A., "Editorial Review: Focusing on dopaminergic stablizers and 5-HT2A receptor antagonists", Current Opinions in CPNS Investigational Drugs, 2000, 22-24, vol. 2, No. 1.
Colpaert, F.C., et al., "Behavioral and 5-HT antagonist effects of ritanserin: A pure and selective antagonist of LSD discrimination in rat", Psychopharmacology, 1985, 45-54, vol. 86.

(Continued)

*Primary Examiner*—Emily Bernhardt
(74) *Attorney, Agent, or Firm*—Stephen G. Kalinchak; Margaret M. Buck

(57) ABSTRACT

The invention relates to compounds of the formula I wherein the variables are as defined in the claims. The compounds are useful in the treatment of a disease where a D4 receptor and/or a 5-HT$_{2A}$ receptor is implicated.

24 Claims, No Drawings

OTHER PUBLICATIONS

Connor, D.F., et al., "Biogenic amines and the psychopharmacology of aggression", Exp. Opin. Ther. Patents, 1998, 349-359, vol. 8, No. 4.

Gazi, L., et al., "The agonist activities of the putative antipsychotic agents, L-745,870 and U-101958 in HEK293 cells expressing the human dopamine D4.4 receptor", Br. J. of Pharmacology, 1998, 889-896, vol. 124.

Gazi, L., et al., "Receptor density as a factor governing the efficacy of the dopamine D4 receptor ligands, L-745,870 and U-101958 at human recombinant D4.4 receptors expressed in CHO cells", Br. J. of Pharmacology, 1999, 613-620, vol. 128.

Gelders, Y. G., "Thymosthenic Agents, A Novel Approach in the Treatment of Schizophrenia", Br. J. of Psychiatry, 1989, 33-36, vol. 155 (suppl. 5).

Hadley, M. S., "D4 Receptors and Their Antagonists", Medicinal Research Reviews, 1996, 507-526, vol. 16, No. 6.

Jentsch, J. D., "Dopamine D4 receptor antagonist reversal of subchronic phencyclidine-induced object retrieval/detour deficits in monkeys", Psychopharmacology, 1999, 78-84, vol. 142.

Leysen, D., et al., "5-HT2 Antagonists: a Concept for the Treatment of Schizophrenia", Current Pharmaceutical Design, 1997, 367-390, vol. 3.

Roth, Bryan, L., et al., "Magic Shotguns Versus Magic Bullets: Selectively Non-Selective Drugs for Mood Disorders and Schizophrenia", Nature Reviews Drug Discovery, Apr. 2004, 353-359, vol. 3.

* cited by examiner

2,3-DIHYDROINDOLE COMPOUNDS

This application claims the benefit of priority under 35 U.S.C. §119(e) of U.S. Provisional Application No. 60/709,174, filed Aug. 17, 2005, the contents of which are hereby incorporated by reference into the subject application.

FIELD OF THE INVENTION

The present invention relates to novel 2,3-dihydroindole compounds having affinity for the dopamine $D_4$ receptor and for the 5-$HT_{2A}$ receptor. The compounds are therefore useful in the treatment of certain psychiatric and neurologic disorders, in particular psychoses.

BACKGROUND OF THE INVENTION

Dopamine $D_4$ receptors belong to the dopamine $D_2$ subfamily of receptors, which is considered to be responsible for the antipsychotic effects of neuroleptics. The characteristic extrapyramidal side effects of neuroleptic drugs, which primarily exert their effect via antagonism of $D_2$ receptors, are known to be due to $D_2$ receptor antagonism in the striatal regions of the brain. However, dopamine $D_4$ receptors are primarily located in areas of the brain other than striatum, suggesting that antagonists of the dopamine $D_4$ receptor will be devoid of extrapyramidal side effects. This is illustrated by the antipsychotic clozapine, which exerts higher affinity for $D_4$ than $D_2$ receptors and is lacking extrapyramidal side effects (Van Tol et al. *Nature* 1991, 350, 610; Hadley *Medicinal Research Reviews* 1996, 16, 507-526, and Sanner *Exp. Opin. Ther. Patents* 1998, 8, 383-393).

A number of $D_4$ ligands, which are postulated to be selective $D_4$ receptor antagonists, (L-745,879 and U-101958), have been shown to posses antipsychotic potential (Mansbach et al. *Psychopharmacology* 1998, 135, 194-200). However, recently it has been reported that these compounds are partial $D_4$ receptor agonists in various in vitro efficacy assays (Gazi et al. *Br. J. Pharmacol.* 1998, 124, 889-896 and Gazi et al. *Br. J. Pharmacol.* 1999, 128, 613-620). Furthermore, it was shown that clozapine, which is an effective antipsychotic, is a silent antagonist (Gazi et al. *Br. J. Pharmacol.* 1999, 128, 613-620).

Consequently, $D_4$ ligands, which are partial $D_4$ receptor agonists or antagonists, may have beneficial effects against psychoses.

Dopamine $D_4$ antagonists may also be useful for the treatment of cognitive deficits (Jentsch et al. *Psychopharmacology* 1999, 142, 78-84).

Furthermore, evidence for a genetic association between the "primarily inattentive" subtype of attention deficit hyperactivity disorder and a tandem duplication polymorphism in the gene encoding the dopamine $D_4$ receptor has been published (McCracken et al. *Mol. Psychiat.* 2000, 5, 531-536). A link between the $D_4$ receptor and attention deficit hyperactivity disorder is further strengthen by published data showing that $D_4$ receptor antagonists counteract the hyperactivity in rats induced by neonatal 6-hydroxydopamine lesions, a preclinical model for this disease (Zhang et al. *Psychopharmacology* 2002, 161, 100-106). This clearly indicates a link between the dopamine $D_4$ receptor and attention deficit hyperactivity disorder, and ligands affecting this receptor may be useful for the treatment of this particular disorder.

Various effects are known with respect to compounds, which are ligands at the different serotonin receptor subtypes. As regards the 5-$HT_{2A}$ receptor, which was previously referred to as the 5-$HT_2$ receptor, the following effects have been reported e.g.:

Antidepressive effect and improvement of the sleep quality (Meert et al. *Drug. Dev. Res.* 1989, 18, 119.), reduction of the negative symptoms of schizophrenia and of extrapyramidal side-effects caused by treatment with classical neuroleptics in schizophrenic patients (Gelders *British J. Psychiatry* 1989, 155 (suppl. 5), 33). Furthermore, selective 5-$HT_{2A}$ antagonists could be effective in the prophylaxis and treatment of migraine (Scrip Report; "Migraine—Current trends in research and treatment"; PJB Publications Ltd.; May 1991) and in the treatment of anxiety (Colpart et al. *Psychopharmacology* 1985, 86, 303-305 and Perregaard et al. *Current Opinion in Therapeutic Patents* 1993, 1, 101-128).

Some clinical studies implicate the 5-$HT_2$ receptor subtype in aggressive behaviour. Furthermore, a typical serotonin-dopamine antagonist neuroleptics have 5-$HT_2$ receptor antagonistic effect in addition to their dopamine blocking properties, and they have been reported to possess anti-aggressive behaviour (Connor et al. *Exp. Opin. Ther. Patents.* 1998, 8(4), 350-351).

Recently, evidence has also accumulated which support the rational for selective 5-$HT_{2A}$ antagonists as drugs capable of treating positive symptoms of psychosis (Leysen et al. *Current Pharmaceutical Design* 1997, 3, 367-390 and Carlsson *Current Opinion in CPNS Investigational Drugs* 2000, 2(1), 22-24).

Accordingly, dopamine $D_4$ receptor ligands are potential drugs for the treatment of schizophrenia and other psychoses, and compounds with combined effects at dopamine $D_4$ and 5-$HT_{2A}$ receptors may have the further benefit of improved effect on positive and negative symptoms in schizophrenia, including depressive and anxiety symptoms.

Dopamine $D_4$ ligands related to the compounds of the invention are known from WO 98/28293. The indane and dihydroindole derivatives disclosed herein have the general formula

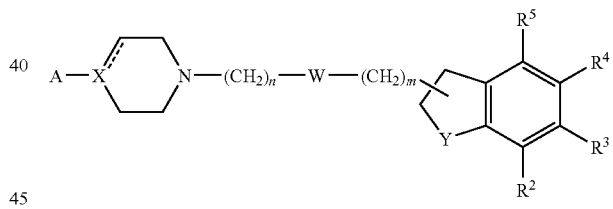

wherein A is an indole and Y is a group completing an indane or a dihydroindole and the other substituents are as defined in the application.

Other dopamine $D_4$ ligands, wherein the indane or dihydroindole is replaced by a pyrrolo[2,3-b]pyridine, a benzimidazole or a furo[2,3-b]pyridine, are described in WO 94/20497, WO 94/22839 and U.S. Pat. No. 5,700,802.

Most lipophilic drugs are mainly eliminated from the body through oxidative metabolism in the liver catalyzed by various cytochrome P450 isoenzymes.

The in vivo hepatic blood-clearance ($CL_b$), considered to be the single most important pharmacokinetic parameter for the drugability of a drug (Bennet, L. The role of pharmacokinetics in the drug development process. Integration of pharmacokinetics, pharmacodynamics, and toxicology in rational drug development, Ed. A. Yacobi et al, Plenum Press, New York, 1993. P. 115-123), may in theory be estimated by calculation from the intrinsic clearance $CL_{int}$, the hepatic blood flow (Q) and the free unbound fraction ($f_u$) of the drug in the blood as $CL_b = (Q*f_u*CL_{int})/(Q+f_u*CL_{int})$. From this follows that drug substances with high measured values for $CL_{int} CL_b$ will in vivo approximate to the hepatic blood flow (Q) resulting in low oral bioavailability and short half-lives.

The intrinsic clearance ($CL_{int}$) is a theoretic measure for the metabolic capacity of a liver when there is no restrictions in blood supply of nutrients, co-factors etc. An in vitro approach for determining values for intrinsic clearance ($CL_{int}$) in humans and animals using in vitro human and animal liver preparations, as described in detail by e.g. Obach, S. et al., The Prediction of Human Pharmacokinetic Parameters from Preclinical and In Vitro Metabolism Data. JPET. Vol. 283, Issue 1, 46-58, 1997, is widely implemented in the pharmaceutical industry and used for evaluating and optimizing drugability of potential drug candidates.

The oral bioavailability and systemic half-life of a compound in vivo are closely related to the blood-clearance, and compounds with higher oral bioavailability and longer half-lives in humans may be sought in a discovery program by optimization on intrinsic clearance ($CL_{int}$), using human liver preparations, for values well below the average human liver blood flow of approximately 1.4 L/min.

One problem associated with some of the above-described compounds is that they possess poor oral bioavailability and that they are too rapidly cleared from the blood resulting in a very short half-live.

SUMMARY OF THE INVENTION

The object of the present invention is to provide compounds that are partial agonists or antagonists at the dopamine $D_4$ receptor, in particular such compounds with combined effects at the dopamine $D_4$ receptors and the 5-$HT_{2A}$ receptor.

Another object is to provide such compounds with an improved pharmacokinetic profile, e.g. higher bioavailability and/or longer half-lives.

Accordingly, the present invention relates to novel compounds of formula I

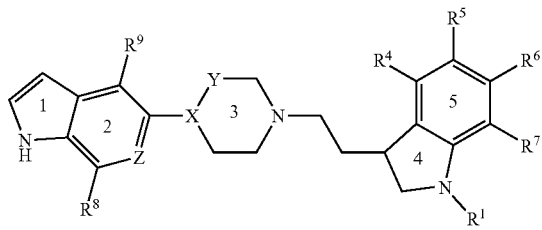

wherein X—Y is selected from N—$CH_2$, C=CH and CH—$CH_2$;
Z is $CR^{10}$ or N;
$R^1$ is A, A' or A"

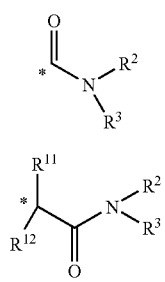

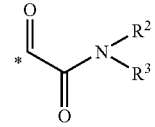

wherein * indicates the atom attached to N via a bond;
$R^2$ and $R^3$ are independently selected from hydrogen and $C_{1-6}$-alkyl;
$R^4$-$R^7$ are independently selected from hydrogen, $C_{1-6}$-alkyl, $C_{1-6}$-alkoxy and halogen;
$R^8$ and $R^9$ are independently selected from hydrogen and halogen;
$R^{10}$ is hydrogen or halogen;
$R^{11}$ and $R^{12}$ are independently selected from hydrogen and $C_{1-6}$-alkyl;

or enantiomers or salts thereof.

In a second aspect the present invention relates to the use of a compound of formula I as defined above for the manufacture of a medicament useful in the treatment of positive, negative and cognitive symptoms of schizophrenia, other psychoses, anxiety disorders, such as generalised anxiety disorder, panic disorder, and obsessive compulsive disorder, depression, aggression, cognitive disorders, side effects induced by conventional antipsychotic agents, migraine, attention deficit hyperactivity disorder and in the improvement of sleep.

In a third aspect the present invention relates to a pharmaceutical composition comprising a compound of formula I as defined above in a therapeutically effective amount together with one or more pharmaceutically acceptable carriers or diluents.

In a fourth aspect the present invention relates to a method of treating a disease where a $D_4$ receptor and/or a 5-$HT_{2A}$ receptor is implicated comprising administration of a therapeutically effective amount of a compound of formula I as defined above.

In a fifth aspect the present invention relates to a method of treating the positive, negative and cognitive symptoms of schizophrenia, other psychoses, anxiety disorders, such as generalised anxiety disorder, panic disorder, and obsessive compulsive disorder, depression, aggression, cognitive disorders, side effects induced by conventional antipsychotic agents, migraine, attention deficit hyperactivity disorder and in the improvement of sleep comprising administration of a therapeutically effective amount of a compound of formula I as defined above.

In a sixth aspect the present invention relates to the use of compounds of the present invention in therapy.

DETAILED DESCRIPTION OF THE INVENTION

In a particular embodiment the present invention relates to compounds of formula I as defined above wherein X—Y is N—$CH_2$.

In another particular embodiment the present invention relates to compounds of formula I as defined above wherein X—Y is C=CH.

In another particular embodiment the present invention relates to compounds of formula I as defined above wherein X—Y is CH—$CH_2$.

In a particular embodiment the present invention relates to compounds of formula I as defined above wherein Z is $CR^{10}$.

In another particular embodiment the present invention relates to compounds of formula I as defined above wherein Z is N.

In a particular embodiment the present invention relates to compounds of formula I as defined above wherein $R^1$ is A

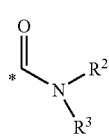

wherein * indicates the atom attached to N via a bond.

In another particular embodiment the present invention relates to compounds of formula I as defined above wherein $R^1$ is A'

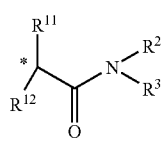

wherein * indicates the atom attached to N via a bond.

In another particular embodiment the present invention relates to compounds of formula I as defined above wherein $R^1$ is A"

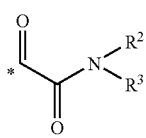

wherein * indicates the atom attached to N via a bond.

In a particular embodiment the present invention relates to compounds of formula I as defined above wherein $R^2$ and $R^3$ are independently selected from hydrogen and $C_{1-6}$-alkyl, preferably methyl.

In another particular embodiment the present invention relates to compounds of formula I as defined above wherein both $R^2$ and $R^3$ are hydrogen.

In a particular embodiment the present invention relates to compounds of formula I as defined above wherein $R^4$-$R^7$ are independently selected from hydrogen, $C_{1-6}$-alkyl, preferably methyl or ethyl, $C_{1-6}$-alkoxy, preferably methoxy and halogen, preferably fluoro.

In another particular embodiment the present invention relates to compounds of formula I as defined above wherein $R^4$-$R^7$ are independently selected from hydrogen and fluoro.

In a more particular embodiment the present invention relates to compounds of formula I as defined above wherein only one of $R^4$-$R^7$, selected from $R^4$, $R^5$ and $R^7$, is different from hydrogen.

In a yet more particular embodiment the present invention relates to compounds of formula I as defined above wherein $R^4$-$R^7$ are all hydrogen.

In a particular embodiment the present invention relates to compounds of formula I as defined above wherein $R^8$ and $R^9$ are independently selected from hydrogen and halogen, preferably fluoro.

In a more particular embodiment the present invention relates to compounds of formula I as defined above wherein both $R^8$ and $R^9$ are hydrogen.

In a particular embodiment the present invention relates to compounds of formula I as defined above wherein $R^{10}$ is hydrogen or halogen, preferably fluoro.

In a more particular embodiment the present invention relates to compounds of formula I as defined above wherein $R^{10}$ is hydrogen.

In a particular embodiment the present invention relates to compounds of formula I as defined above wherein $R^{11}$ and $R^{12}$ are independently selected from hydrogen and $C_{1-6}$-alkyl, preferably methyl or ethyl.

In a more particular embodiment the present invention relates to compounds of formula I as defined above wherein both $R^{11}$ and $R^{12}$ are hydrogen.

In a particular embodiment the present invention relates to compounds of formula I, wherein $R^2$ and $R^3$ are both hydrogen; $R^4$, $R^5$, $R^6$ and $R^7$ are independently selected from hydrogen, methyl, fluor and methoxy; and $R^8$, $R^9$, $R^{10}$, $R^{11}$ and $R^{12}$ are all hydrogen. Within this embodiment, particular mentioning is made of X—Y representing N—$CH_2$ and of Z representing $CR^{10}$.

Particular compounds of the invention are compounds selected from:
  (+)-(S)-3-{2-[4-(1H-Indol-5-yl)-piperazin-1-yl]-ethyl}-2,3-dihydro-1H-indole-1-carboxylic acid amide;
  (+)-3-{2-[4-(1H-Indol-5-yl)-piperazin-1-yl]-ethyl}-2,3-dihydro-5-fluoro-1H-indole-1-carboxylic acid amide;
  (+)-(S)-3-{2-[4-(1H-Pyrrolo[2,3-c]pyridin-5-yl)-piperazin-1-yl]-ethyl}-2,3-dihydro-1H-indole-1-carboxylic acid amide;
  (+)-3-{2-[4-(1H-Pyrrolo[2,3-c]pyridin-5-yl)-piperazin-1-yl]-ethyl}-2,3-dihydro-5-fluoro-1H-indole-1-carboxylic acid amide;
  (RS)-3-{2-[4-(1H-Indol-5-yl)-piperazin-1-yl]-ethyl}-2,3-dihydro-1H-indole-1-carboxylic acid amide;
  2-((+)-(S)-3-{2-[4-(1H-Indol-5-yl)-piperazin-1-yl]-ethyl}-2,3-dihydro-1H-indol-1-yl)-acetamide;
  2-((+)-3-{2-[4-(1H-Indol-5-yl)-piperazin-1-yl]-ethyl}-2,3-dihydro-5-fluoro-1H-indol-1-yl)-acetamide;
  2-((+)-(S)-3-{2-[4-(1H-Pyrrolo[2,3-c]pyridin-5-yl)-piperazin-1-yl]-ethyl}-2,3-dihydro-1H-indol-1-yl)-acetamide;
  2-((−)—(R)-3-{2-[4-(1H-Indol-5-yl)-piperazin-1-yl]-ethyl}-2,3-dihydro-1H-indol-1-yl)-acetamide;
  2-((RS)-3-{2-[4-(1H-Indol-5-yl)-piperazin-1-yl]-ethyl}-2,3-dihydro-1H-indol-1-yl)-acetamide;
  2-((+)-(S)-3-{2-[4-(7-Fluoro-1H-indol-5-yl)-piperazin-1-yl]-ethyl}-2,3-dihydro-1H-indol -1-yl)-acetamide;
  2-((RS)-3-{2-[4-(1H-Indol-5-yl)-piperazin-1-yl]-ethyl}-4-methyl-2,3-dihydro-1H-indol -1-yl)-acetamide;
  2-((RS)-3-{2-[4-(1H-Indol-5-yl)-piperazin-1-yl]-ethyl}-7-methoxy-2,3-dihydro-1H-indol -1-yl)-acetamide;
  2-((+)-(S)-3-{2-[4-(1H-Indol-5-yl)-piperazin-1-yl]-ethyl}-2,3-dihydro-1H-indol-1-yl)-N-methyl-acetamide;
  N-Methyl-2-((+)-(S)-3-{2-[4-(1H-pyrrolo[2,3-c]pyridin-5-yl)-piperazin-1-yl]-ethyl}-2,3-dihydro-1H-indol-1-yl)-acetamide;
  (RS)-2—((S)-3-{2-[4-(1H-Indol-5-yl)-piperazin-1-yl]-ethyl}-2,3-dihydro-1H-indol-1-yl)-propionamide;

2-((+)-(S)-3-{2-[4-(1H-Indol-5-yl)-piperazin-1-yl]-ethyl}-2,3-dihydro-1H-indol-1-yl)-N,N-dimethyl-acetamide;

2-((+)-(S)-3-{2-[4-(1H-Indol-5-yl)-3,6-dihydro-2H-piperidin-1-yl]-ethyl}-2,3-dihydro-1H-indol-1-yl)-acetamide;

2-((+)-(S)-3-{2-[4-(1H-Indol-5-yl)-piperidin-1-yl]-ethyl}-2,3-dihydro-1H-indol-1-yl)-acetamide;

2-((+)-(S)-3-{2-[4-(1H-Indol-5-yl)-piperazin-1-yl]-ethyl}-2,3-dihydro-1H-indol-1-yl)-2-oxo-acetamide;

2-Oxo-2-((+)-(S)-3-{2-[4-(1H-pyrrolo[2,3-c]pyridin-5-yl)-piperazin-1-yl]-ethyl}-2,3-dihydro-1H-indol-1-yl)-acetamide;

2-((+)-(S)-3-{2-[4-(1H-Indol-5-yl)-piperidin-1-yl]-ethyl}-2,3-dihydro-1H-indol-1-yl)-2-oxoacetamide;

2-((RS)-3-{2-[4-(1H-Indol-5-yl)-piperazin-1-yl]-ethyl}-7-methoxy-2,3-dihydro-1H-indol-1-yl)-2-oxo-acetamide;

(+)-(S)-3-{2-[4-(1H-Indol-5-yl)-3,6-dihydro-2H-pyridin-1-yl]-ethyl}-2,3-dihydro-1H-indole-1-carboxylic acid amide; and (+)-(S)-3-{2-[4-(1H-Indol-5-yl)-piperidin-1-yl]-ethyl}-2,3-dihydro-1H-indole-1-carboxylic acid amide;

or salts thereof.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, and 2-methyl-1-propyl.

The term $C_{1-6}$-alkoxy designates such groups in which the alkyl group is $C_{1-6}$-alkyl as defined above.

Halogen means fluoro, chloro, bromo or iodo.

The present invention also comprises salts of the compounds of the invention, typically, pharmaceutically acceptable salts. The salts of the invention include acid addition salts, metal salts, ammonium and alkylated ammonium salts.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspect of the invention. The patient to be treated, i.e. the patient in need thereof, is preferably a mammal, in particular a human being.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in *J. Pharm. Sci.* 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any isomers (i.e. enantiomers or diastereomers), as separated, pure or partially purified and any mixtures thereof including racemic and diastereomeric mixtures, i.e. a mixture of stereoisomers, are included within the scope of the invention.

Racemic forms can be resolved into the optical antipodes by known methods, for example, by fractional separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, by stereoselective synthesis or by enzymatic resolution.

The pharmaceutical compositions of this invention, or those which are manufactured in accordance with this invention, may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used. Tablets may be prepared by mixing the active ingredient with ordinary adjuvants and/or diluents and subsequently compressing the mixture in a conventional tabletting machine. Examples of adjuvants or diluents comprise:

corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilizing the solution and filling it in suitable ampules or vials. Any suitable additive conventionally used in the art may be added, such as tonicity agents, preservatives, antioxidants, etc.

Conveniently, the compounds of the invention are preferably formulated in a unit dosage form, each dosage containing from about 0.01 to about 8000 mg, preferably from about 0.05 to about 5000 and more preferred from about 0.1 to about 1000 mg, the actual dosage may however vary e.g. according to the specific compound. The term "unit dosage form" refers to physically discrete units suitable as unitary dosages for human subjects and other mammals, each unit containing a predetermined quantity of active material calculated to produce the desired therapeutic effect, in association with one or more pharmaceutically acceptable carriers, diluents, excipients or other additives normally used in the art.

The compounds of the invention are effective over a wide dosage range. For example, dosages per day normally fall within the range of about 0.01 to about 100 mg/kg of body weight, preferably within the range of about 0.1 to about 75 mg/kg. However, it will be understood that the amount of the compound actually administered will be determined by a physician, according to the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The compounds of the invention are prepared by the following general methods:

1) Alkylating a piperazine, piperidine or tetrahydropyridine of formula II with an alkylating derivative of formula III:

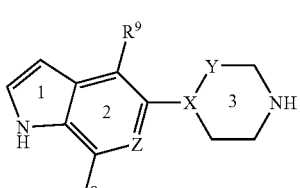

II

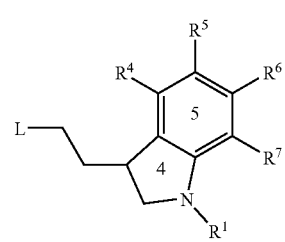

III wherein $R^1$, $R^4$-$R^9$, X—Y and Z are as previously defined, and L is a leaving group such as e.g. halogen, mesylate or tosylate 2) Introduction of $R^1$ at the indoline nitrogen atom of formula IV by e.g. alkylation, acylation or carbamoylation:

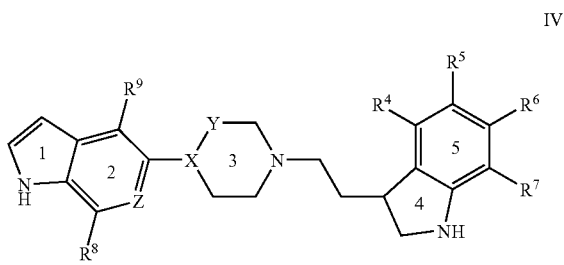

IV wherein $R^4$-$R^9$, X—Y and Z are as previously defined, by the use of an alkylating agent, an activated ester, an acid chloride, a carboxylic acid and a coupling reagent 3) Reduction of the pyridinium halide of formula V:

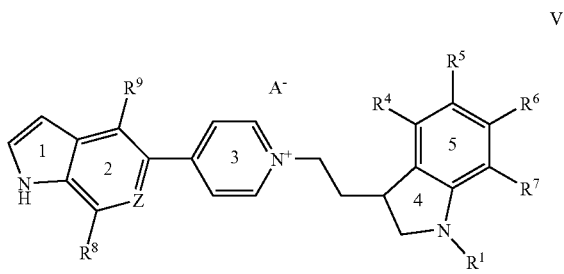

V wherein $R^1$, $R^4$-$R^9$ and Z are as previously defined and $A^-$ is a negatively charged counter ion such as e.g. a halide, by the use of a reducing agent such as e.g. sodium borohydride 4) Reduction of the tetrahydropyridine of formula VI:

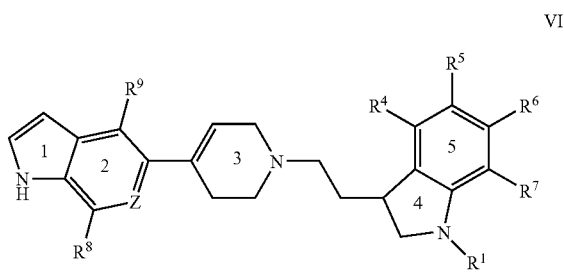

VI wherein $R^1$, $R^4$-$R^9$ and Z are as previously defined under reducing conditions such as e.g. hydrogenation in the presence of e.g. palladium; whereupon the compound of formula I is isolated as the free base or a pharmaceutical acceptable acid addition salt thereof.

Alkylation according to method 1) and 2) is conveniently performed in an inert organic solvent such as a suitably boiling alcohol or ketone, preferably in the presence of an organic or inorganic base (potassium carbonate, diisopropylethylamine or triethylamine) at reflux temperature. Alternatively, the alkylation can be performed at a fixed temperature, which is different from the boiling point, in one of the above-mentioned solvents or in dimethyl formamide (DMF), dimethyl-sulfoxide (DMSO) or N-methylpyrrolidin-2-one (NMP), preferably in the presence of a base. In some cases it is an advantage to add e.g. potassium iodide to the reaction mixture.

Piperazines of formula II are e.g. prepared from nitroindoles or substituted nitroindoles by reduction of the nitro group to the corresponding aniline. The aniline is then converted into a piperazine by methods obvious to a chemist skilled in the art (see e.g. Kruse et al. *Red. Trav. Chim. Pays. Bas.* 1988 107, 303-309 and WO 98/28293). Furthermore, piperazines of formula II are prepared from properly substituted nitro- or amino-2,3-dihydro-1H-indoles, which subsequently are oxidized to their corresponding indoles and subjected to piperazine synthesis as described above, or alternatively, which subsequently are subjected to piperazine synthesis as described above and oxidized to their corresponding indoles. The tetrahydropyridines are prepared by the method described in WO 94/20459, whereas the corresponding piperidines are prepared from the corresponding tetrahydropyridines by reduction of the double bond by e.g. hydrogenation.

The alkylating derivatives of formula III are described in the literature (see e.g. WO 98/28293) or by analogous methods.

Compounds of formula IV are prepared by method 1), where $R_1$ is a protecting group. $R_1$ is e.g. an acetyl or a boc group, which can be removed under acidic and/or alkaline condition.

Compounds of formula V are prepared by alkylation of 5-(pyridin-4-yl)-1H-indoles with alkylating derivatives of formula III, e.g. in 1,4-dioxane or in a ketone. The 5-(pyridin-4-yl)-1H-indoles are prepared by e.g. palladium catalyst cross coupling of an N-protected 5-halo-1H-indole with e.g. pyridine-4-boronic acid in an appropriate solvent.

Compounds of formula VI are prepared as described in method 3).

Experimental Section

LC-MS

General: Solvent system: A=water/TFA (100:0.05) and B=water/acetonitrile/TFA (5:95:0.035) (TFA=trifluoroacetic acid). Retention times (RT) are expressed in minutes. MS instruments are from PESciex (API), equipped with APPI-source and operated in positive ion mode.

Method A: API 150EX and Shimadzu LC8/SLC-10A LC system. Column: 30×4.6 mm Waters Symmetry C18 with 3.5 µM particles operated at room temperature. Linear Gradient elution with 90% A to 100% B in 4 min and a flow rate of 2 ml/min.

Method B: API 150EX and Shimadzu LC10AD/SLC-10A LC system. Column: 30×4.6 mm Waters Atlantis dC18 with 3 µM particles operated at 60° C. Linear Gradient elution with 98% A to 100% B in 2.4 min and a flow rate of 3.3 ml/min.

Method C: API 300 and Shimadzu LC10ADvp/SLC-10Avp LC system. Column: 30×4.6 mm Waters Atlantis dC18 with 3 µM particles operated at 60° C. Linear Gradient elution with 98% A to 100% B in 1.6 min and a flow rate of 5.2 ml/min.

Optical Rotation

Optical rotation was as standard performed as a single determination at a concentration of 1% of compound on a Perkin Elmer Polarimeter model 241 apparatus, using the Na 589 nm Spectral Line for the measurements. As standard, the experiment was done at ambient temperature and in dimethyl sulfoxide.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein. The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Preparation of Intermediates

A. Amines and pyridines 5-(Piperazin-1-yl)-1H-indole

A mixture of 5-nitro-1H-indole (34 g), palladium (5 wt %, dry basis) on activated carbon (2.5 g) and ethyl acetate was shaken at room temperature for 1.5 h under 3 atmospheres of hydrogen. The mixture was filtered, and the solvent was removed in vacuo to yield a solid (28 g), which was dissolved in tetrahydrofuran (400 mL). This solution was added to a boiling mixture of N-benzyliminodiacetic acid (54.4 g) and 1,1'-carbonyldiimidazole (82.4 g) in tetrahydrofuran (1100 mL), and the resulting mixture was boiled under reflux for 3 h. The mixture was filtered and concentrated in vacuo. The residue was purified by flash chromatography on silicagel (eluent: ethyl acetate/triethylamine 100:4) to give a solid (57.5 g), which subsequently was suspended in tetrahydrofuran (300 mL) and added to alane in tetrahydrofuran (500 mL) at 5-16° C. The alane was prepared from lithium aluminium hydride (25 g) and 96% sulphuric acid (32.3 g). The mixture was stirred at 5° C. for 45 min and subsequently quenched by addition of water (50 mL), 15% aqueous sodium hydroxide solution (25 mL) and water (125 mL). The mixture was dried ($MgSO_4$), filtered and concentrated in vacuo. The residue was purified by flash chromatography on silicagel (eluent: ethyl acetate) to give a brown oily compound (44.9 g), which subsequently was dissolved in methanol (1000 mL). Ammonium formate (150 g) and palladium (5 wt %, dry basis) on activated carbon (12 g) was added, and the mixture was boiled under reflux for 45 min, cooled, filtered and concentrated in vacuo. The residue was dissolved in tetrahydrofuran/ethyl acetate and poured onto brine. Concentrated aqueous ammonia solution was added to the mixture under cooling to give an alkaline reaction mixture. The two phases were separated, and the aqueous phase was extracted twice with tetrahydrofuran/ethyl acetate. The combined organic phases were washed with brine, dried ($MgSO_4$) and concentrated in vacuo. The residue was precipitated from tetrahydrofuran/heptane to give the title compound (17.3 g).

5-(3,6-Dihydro-2H-pyridin-4-yl)-1H-indole 5-(3,6-Dihydro-2H-pyridin-4-yl)-1H-indole was prepared as described in WO 94/20459.

5-(Piperidin-4-yl)-1H-indole

A mixture of 5-(3,6-dihydro-2H-pyridin-4-yl)-1H-indole (3.4 g), platinum oxide (0.2 g) and acetic acid (50 mL) was shaken at room temperature for 24 h and under 3 atmospheres of hydrogen. The mixture was filtered, and the solvent was removed in vacuo. The residue was purified by flash chromatography on silicagel (eluent: 4 M ammonia in methanol) to give the title compound (1.3 g).

5-(piperazin-1-yl)-1H-pyrrolo[2,3-c]pyridine

To a solution of ethyl piperazine-1-carboxylate (80.7 g, 0.51 mol) in ethanol (500 mL) was added a solution of 2-chloro-4-methyl-5-nitropyridine (22 g, 0.13 mol) in ethanol (500 mL). The resulting mixture was stirred at room temperature for 3 days and filtered. The filter cake was washed with diisopropyl ether to give a yellow powder (38.2 g). This compound was mixed with N,N-dimethyl formamide dimethylacetal (86 mL, 0.65 mol) and dimethyl formamide (450 mL), and the resulting mixture was heated at 90° C. for 3 days. The mixture was poured onto brine and extracted with tetrahydrofuran. The combined organic phase was washed with brine, dried ($MgSO_4$), filtered and concentrated in vacuo. The residue was precipitated from a mixture of tetrahydrofuran/ethyl acetate/heptane (38.9 g). This compound (27.1 g, 0.78 mol) was dissolved in tetrahydrofuran (600 mL) and ethanol (50 mL), and acetic acid (10 mL) and palladium (5 wt %, dry basis) on activated carbon (4.0 g) was added. The mixture was hydrogenated at 3 bar for 4 h and filtered. Triethylamine (25 mL) was added to the filtrate, and the resulting mixture was concentrated in vacuo. The residue was purified by flash chromatography (ethyl acetate) to give a syrup (19.8 g). The syrup (18.3 g) was dissolved in ethanol (240 mL), and a solution of potassium hydroxide (22.5 g, 0.4 mol) in water (60 mL) was added to this solution. The resulting mixture was boiled under reflux for 48 h, reduced in vacuo (100 mL) and brine was added. The aqueous mixture was extracted with tetrahydrofuran. The combined organic phase was washed with brine, treated with activated carbon, dried ($MgSO_4$), filtered and concentrated in vacuo (11.6 g). The residue was precipitated from tetrahydrofuran/methanol to give the title compound (8.0 g).

5-(Pyridin-4-yl)-1H-indole

A mixture of pyridine-4-boronic acid (5.0 g, 0.041 mol), tert-butyl 5-bromo-indole-1-carboxylate (11.8 g, 0.04 mol), 2 M aqueous sodium carbonate (80 mL, 0.16 mol), tetrakis (triphenylphosphine)palladium(0) (0.92 g, 0.0008 mol), ethanol (19 mL) and toluene (175 mL) was boiled under reflux for 12 h. The experiment was repeated with the double amount of starting materials, e.g. 10 g of pyridine-4-boronic acid. The combined reaction mixture from the two experiments was poured onto a saturated sodium chloride solution (brine), and the aqueous phase was extracted with ethyl acetate. The combined organic phase was washed with brine, dried ($MgSO_4$), filtered and concentrated in vacuo. The residue was purified by flash chromatography (ethyl acetate followed by ethyl acetate/triethylamine 95:5) to give tert-butyl 5-pyridin-4-yl-indole-1-carboxylate (25.5 g, 61%), which was dissolved in a mixture of methanol (500 mL), tetrahydrofuran (200 mL) and 15% aqueous sodium hydroxide (25 mL). The mixture was boiled under reflux for 1 h, concentrate in vacuo to 200 mL and poured onto brine. The aqueous phase was extracted with a mixture of ethyl acetate and tetrahydrofuran, and the combined organic phase was washed with brine, dried ($MgSO_4$), filtered and concentrated in vacuo. The residue was precipitated from a cold mixture of methanol and tetrahydrofuran to give the title compound as a creamy solid (9.5 g, 54%). A second crop of the title compound was obtained from the mother liquor (1.7 g, 9%).

7-Fluoro-5-(piperazin-1-yl)-1H-indole

To a mixture of 7-fluoro-1H-indole (18.5 g, 0.14 mol), borane trimethylamine complex (80 g, 1.1 mol) and 1,4-dioxane (700 mL) was, over a periode of 15 min, added a 37% aqueous HCl (80 mL) solution. The resulting solution reached a maximum temperature of 40° C., and the solution was subsequent stirred at room temperature for another 16 h. The mixture was boiled under reflux for 1 h, 6 M aqueous HCl (500 mL) was added, and the resulting mixture was boiled under reflux for another 15 min. The solution was concentrated at atmospheric pressure and poured onto a mixture of ice and brine. The aqueous phase was made alkaline by the use of 25% aqueous ammonia and extracted with ethyl acetate. The combined organic phase was dried ($MgSO_4$), filtered and concentrated in vacuo. The residue was dissolved in a mixture of triethylamine (38 mL, 0.27 mol) and tetrahydrofuran (350 mL) and cooled to 10° C. Acetyl Chloride (11.2 g, 0.14 mol) was added to the mixture, which thereafter was filtered and concentrated in vacuo. The residue was purified by flash chromatography (ethyl acetate/heptane 50:50) to give 1-(7-fluoro-2,3-dihydro-1H-indol-1-yl-ethanone (16.7 g, 0.09 mol), which was dissolved in acetic acid (250 mL). To this mixture was added 100% nitric acid (5.8 ml, 0.14 mol) over a period of 5 min, and the resulting mixture was stirred at room temperature for 2 h. The reaction was not run to completion, and an additional amount of 6 mL of 100% nitric acid was added. Another 6 mL of 100% nitric acid was added and the mixture was stirred at room temperature for 16 h. The mixture was poured onto a mixture of ice and brine. The aqueous phase was made alkaline by the use of 25% aqueous ammonia and extracted with ethyl acetate. The combined organic phase was washed with brine, dried ($MgSO_4$), filtered and concentrated in vacuo. The residue was crystallised from a mixture of ethyl acetate and 2-propanol to give 1-(7-fluoro-5-nitro-2,3-dihydro-1H-indol-1-yl)-ethanone (15.9 g), which was dissolved in methanol (500 mL). To this solution was added ammonium formate (44.4 g, 0.7 mol) and palladium (5 wt %, dry basis) on activated carbon (4.0 g), and the mixture was boiled under reflux for 30 min. The mixture was cooled in an ice bath, filtered and concentrated in vacuo. The residue was dissolved in methanol (100 mL) and ethyl acetate (500 mL), and ammonium formate precipitated out of solution and was removed by filtration. The mother liquor was concentrated in vacuo, and the residue was purified by flash chromatography (ethyl acetate/heptane 65:35) to give 1-(5-amino-7-fluoro-2,3-dihydro-1H-indol-1-yl)-ethanone (13.1 g, >91%). The compound was dissolved in methanol (350 mL), 28% aqueous sodium hydroxide (100 mL) and water (100 mL), and the resulting mixture was boiled under reflux for 4 h. The reaction mixture was concentrated to a volume of about 200 mL, and brine (1 L) was added. The aqueous phase was extracted with a mixture of ethyl acetate and tetrahydrofuran. The combined organic phase was washed with brine, dried ($MgSO_4$), filtered and concentrated in vacuo to give 7-fluoro-2,3-dihydro-1H-indol-5-ylamine (11.0 g, 96%). This compound was dissolved in p-xylene (500 mL), and palladium (5 wt %, dry basis) on activated carbon (7.5 g) was added. The resulting mixture was boiled under reflux by the use of a Dean/Stark trap for 1.5 h, cooled and filtered. The filter cake was washed with ethyl acetate and tetrahydrofuran, and the organic phases were combined and concentrated in vacuo. The residue was purified by flash chromatography (ethyl acetate/heptane 50:50) to give 7-fluoro-1H-indol-5-ylamine (3.3 g, 29%). A further batch of 7-fluoro-1H-indol-5-ylamine was prepared (0.2 g), and the combined batch was used in the following. A mixture of N-benzyliminodiacetic (5.9 g, 0.027 mol), 1,1'-carbonyldiimidazole (9.0 g, 0.056 mol) and tetrahydrofuran (175 mL) was boiled under reflux for 30 min. To this solution was added a solution of 7-fluoro-1H-indol-5-ylamine (3.47 g, 0.023 mol) in tetrahydrofuran (75 mL) over a period of 1 h. The resulting mixture was boiled under reflux for 3 h and concentrated in vacuo to 50 mL. This solution was purified by flash chromatography (ethyl acetate/heptane 80:20) to give 4-benzyl-1-(7-fluoro-1H-indol-5-yl)piperazine-2,6-dione (7.8 g, 95%), which was dissolved in tetrahydrofuran (75 mL) and subsequently added drop wise to a solution of alane in tetrahydrofuran over 60 min at 5-10° C. The resulting mixture was stirred at 7° C. for 30 min and then quenched by addition of water (6.5 mL), 15% aqueous sodium hydroxide (3.25 mL) and water (16 mL). $MgSO_4$ was added to the mixture, which was filtered and concentrated in vacuo. The residue was purified by flash chromatography (ethyl acetate/heptane 50:50) to give 5-(4-benzylpiperazin-1-yl)-7-fluoro-1H-indole (4.9 g, 63%). The alane was prepared as described in the following: Lithium aluminium hydride (3.23 g, 0.085 mol) was suspended in tetrahydrofuran (100 mL), and the mixture was cooled to 6° C. To this suspension was added a mixture of 96% sulphuric acid in tetrahydrofuran (75 mL) over 30 min at 5-11° C. The resulting mixture was stirred for 1 h at 5-7° C. to give alane in tetrahydrofuran.

A mixture of 5-(4-benzylpiperazin-1-yl)-7-fluoro-1H-indole (4.9 g, 0.016 mol), ammonium formate (16.0 g, 0.25 mol), palladium (5 wt %, dry basis) on activated carbon (2.0 g) and methanol (100 mL) was boiled under reflux for 2 h. The mixture was cooled, filtered and concentrated in vacuo. The residue was dissolved in 25% aqueous ammonia (50 mL) and brine, and the aqueous phase was extracted with a mixture of ethyl acetate and tetrahydrofuran. The combined organic phase was washed with brine, dried ($MgSO_4$), filtered and concentrated in vacuo. The residue was crystallized from a mixture of tetrahydrofuran, ethyl acetate and diisopropyl ether to give the title compound (1.6 g, 42%).

B. Alkylating Reagents

Methyl (RS)-(2,3-Dihydro-1H-indol-3-yl)acetate

A mixture of commercially available (1H-indol-3-yl)acetic acid (200 g, 1.14 mol), methanol (2700 mL) and a saturated solution of HCl in diethyl ether (750 mL) was stirred at room temperature for 16 h. The solvent was removed in vacuo, and the residue was subjected to aqueous work-up under alkaline conditions by the use of aqueous ammonia to yield methyl (1H-indol-3-yl)acetate as an oil (202.5 g, 94%). The crude oil was dissolved in acetic acid (2 L), and sodium cyanoborohydride (60 g, 0.95 mol) was added in portions of 1 g over a period of 8 h. The resulting mixture was stirred at room temperature for 16 h and then poured onto an ice/water mixture. Aqueous work-up under alkaline conditions gave the crude product that was purified by flash chromatography (ethyl acetate/heptane 1:1) to give the title compound (97.3 g, 48%).

Ethyl (RS)-(2,3-Dihydro-5-fluoro-1H-indol-3-yl) acetate

A mixture of ethyl (5-fluoro-1H-indol-3-yl)acetate (Bullock et al. J. Am. Chem. Soc. 1951, 73, 5155-5157) (72.5 g, 0.33 mol), 70% methane sulfonic acid (aq) (50 mL) and palladium (5 wt %, dry basis) on activated carbon (20 g) in ethanol (700 mL) was treated with hydrogen at 3 bar and 50° C. for 48 h. The mixture was filtered and concentrated in vacuo. The residue was dissolved in ethyl acetate, and aqueous ammonia was added. The phases were separated, and the aqueous phase was extracted twice with ethyl acetate. The combined organic phase was washed with brine, dried ($MgSO_4$) and concentrated in vacuo (55 g, 75%).

Methyl (RS)-(1-tert-Butoxycarbonyl-2,3-dihydro-1H-indol-3-yl)acetic acid

Methyl (RS)-(2,3-Dihydro-1H-indol-3-yl)acetate (97.2 g, 0.51 mol) was dissolved in tetrahydrofuran (1000 mL), and a solution of di-tert-butyl dicarbonate (118.2 g, 0.54 mol) in tetrahydrofuran (500 mL) was added. The resulting mixture was stirred at room temperature for 16 h and poured into water. The aqueous phase was extracted with diethyl ether, and the combined organic phase was washed with brine and dried ($MgSO_4$). The organic solvent was removed in vacuo, and the oily residue was purified by flash chromatography (heptane/ethyl acetate 2:1) to give crude title compound (148 g, 100%).

Ethyl (RS)-(1-tert-Butoxycarbonyl-2,3-dihydro-5-fluoro-1H-indol-3-yl)acetic acid was prepared in a similar manner starting from ethyl (RS)-(2,3-dihydro-5-fluoro-1H-indol-3-yl)acetate.

(+)-(1-tert-Butoxycarbonyl-2,3-dihydro-1H-indol-3-yl)acetic acid

Methyl (RS)-(1-tert-Butoxycarbonyl-2,3-dihydro-1H-indol-3-yl)acetic acid (50 g, 0.17 mol) was mixed with Candida Antarctica Lipase (CAL, SP-435, Novo Nordisk, Denmark) (2.5 g) and subsequently added 0.1 M phosphate buffer (pH=7.0) (3 L) under vigorous stirring. The resulting mixture was stirred vigorously at 25° C. for 120 h, and the pH was maintained at 7 by the addition of 0.5 N NaOH. After addition of about 0.45 equivalent of base, filtering off the enzyme stopped the reaction. The enzyme was washed with diethyl ether (1 L), and the pH of the aqueous phase was adjusted to 8. The aqueous phase was extracted with diethyl ether (2×1 L), and the combined organic extracts were dried ($MgSO_4$) and concentrated in vacuo to give crude methyl (R)-(1-tert-butoxycarbonyl-2,3-dihydro-1H-indol-3-yl)acetic acid, which was used for the synthesis of (−)-(R)-(1-tert-butoxycarbonyl-2,3-dihydro-1H-indol-3-yl)acetic acid (see below). The aqueous phase was cooled by addition of ice, and the pH adjusted to 1.5 with 37% HCl (aq). The aqueous phase was extracted with diethyl ether (3×1 L), and the combined organic extracts were dried ($MgSO_4$) and concentrated in vacuo to give crude title compound (enantiomeric excess was about 80-85%). A number of precipitations from diisopropyl ether gave the title compound: mp 137-138° C.; enantiomeric excess 96.5%; $[\alpha]_D$=+12.8° (c=0.45, methanol). The chiral analysis was performed on a Ultron ES OVM 150×4.6 mm, flow 1.0 ml/min, eluent 25 mM phosphate buffer (pH≅4.6)/methanol/2-propanol/tetrahydrofuran 90/5/5/0.5, T=30° C. Enantiomeric purities expressed as enantiomeric excess (ee) were calculated from peak areas.

(+)-(1-tert-Butoxycarbonyl-2,3-dihydro-1H-indol-3-yl) acetic acid was assigned as the (S)-enantiomer, as the dihydrogen phosphate salt of 2-(2,3-dihydro-1H-indol-3-yl)ethanol (obtained as described below from (+)-(1-tert-butoxycarbonyl-2,3-dihydro-1H-indol-3-yl)acetic acid) was measured as the (+)-enantiomer (Frydenvang et al. *Chirality* 2004, 16, 126-130).

The following compound was prepared in a similar manner:

(+)-(1-tert-Butoxycarbonyl-2,3-dihydro-5-fluoro-1H-indol-3-yl)acetic acid from ethyl (RS)-(1-tert-butoxycarbonyl-2,3-dihydro-5-fluoro-1H-indol-3-yl)acetic acid. Assignment of the optical rotation was done in methanol.

(−)-(1-tert-Butoxycarbonyl-2,3-dihydro-1H-indol-3-yl)acetic acid

Crude methyl (R)-(1-tert-butoxycarbonyl-2,3-dihydro-1H-indol-3-yl)acetic acid (33.7 g, 0.116 mol) was treated with CAL enzyme and subsequently subjected to work-up as described above for the synthesis of the (+)-(S)-enantiomer. The residue, which was further enriched in the (R)-enantiomer, was purified by flash chromatography and dissolved in a mixture of ethanol (500 ml) and 1 N NaOH (500 ml). The resulting mixture was stirred at room temperature for 30 min, and the ethanol was removed in vacuo. The aqueous phase was washed with diethyl ether, cooled by the addition of ice, and the pH was adjusted to 1. The aqueous phase was extracted with diethyl ether (3×400 mL), and the combined organic extracts were washed with brine, dried ($MgSO_4$), and the solvent was removed in vacuo (31 g, enantiomeric excess: 94.6%). The residue was precipitated from diisopropyl ether (50 ml) to give the title compound (26 g): mp 136-137° C.; enantiomeric excess 97.7%; $[\alpha]_D$=−12.6° (c=0.47, methanol). The chiral analysis was performed on a Ultron ES OVM 150×4.6 mm, flow 1.0 mL/min, eluent 25 mM phosphate buffer (pH≅4.6)/methanol/2-propanol/tetrahydrofuran 90/5/5/0.5, T=30° C. Enantiomeric purities expressed as enantiomeric excess (ee) were calculated from peak areas.

Methyl (S)-(2,3-Dihydro-1H-indol-3-yl)acetate (+)-(S)-(1-tert-Butoxycarbonyl-2,3-dihydro-1H-indol-3-yl)acetic acid (14.2 g, 0.05 mol) was dissolved in methanol (600 mL), cooled (5° C.) and a saturated solution of HCl in diethyl ether (150 mL) was added. The resulting mixture was stirred at room temperature for 16 h, concentrated in vacuo to about 50 mL and poured onto an ice/water mixture. The aqueous phase was extracted with ethyl acetate and diethyl ether, and the combined organic phases were washed with aqueous ammonia and brine. The organic phase was dried and concentrated in vacuo to give the title compound (9.8 g, 100%).

The following compounds were prepared in a similar manner:

Methyl (R)-(2,3-Dihydro-1H-indol-3-yl)acetate from (−)-(R)-(1-tert-butoxycarbonyl-2,3-dihydro-1H-indol-3-yl)acetic acid.

Methyl (R) or (S)-(2,3-Dihydro-5-fluoro-1H-indol-3-yl)acetate (enantiomer A)

from (+)-(1-tert-butoxycarbonyl-2,3-dihydro-5-fluoro-1H-indol-3-yl)acetic acid.

(RS)-2-(2,3-Dihydro-1H-indol-3-yl)ethanol

Methyl (RS)-(2,3-Dihydro-1H-indol-3-yl)acetate (30.0 g, 0.16 mol) was dissolved in tetrahydrofuran (500 mL) and subsequently added to a suspension of lithium aluminium hydride (10.6 g, 0.28 mol) in tetrahydrofuran (500 mL) over a period of 75 min at 33-39° C. The reaction was quenched by sequential addition of water (20 mL), 15% NaOH (10 mL) and water (50 mL), and then $MgSO_4$. The mixture was stirred at room temperature for 1 h, filtered and concentrated in vacuo to give the title compound (24.2 g, 95%).

The following compounds were prepared in a similar manner:

(S)-2-(2,3-Dihydro-1H-indol-3-yl)ethanol from methyl (S)-(2,3-dihydro-1H-indol-3-yl)acetate (R)-2-(2,3-Dihydro-1H-indol-3-yl)ethanol from methyl (R)-(2,3-dihydro-1H-indol-3-yl)acetate (R) or (S)-2-(2,3-Dihydro-5-fluoro-1H-indol-3-yl)ethanol from methyl (R) or (S)-(2,3-dihydro-5-fluoro-1H-indol-3-yl)acetate (enantiomer A)

(RS)-2-(4-Methyl-2,3-dihydro-1H-indol-3-yl)ethanol

A mixture of 4-methyl-1H-indole (15.7 g, 0.12 mol), diethyl ether (300 mL) and tetrahydrofuran (300 mL) was stirred at room temperature. To this solution was added oxalyl chloride (22.8 g, 0.18 mol) drop wise. The resulting solution was stirred at room temperature for 16 h. Ethanol (100 mL) was added, and the mixture was stirred for 5 min. Triethylamine (100 mL) was added under cooling (20-30° C.) and then ice (200 mL) and brine (1 L). The aqueous phase was extracted with ethyl acetate, and the combined organic phase was washed with brine, dried ($MgSO_4$) and concentrated in vacuo. The solid compound formed was stirred with diethyl ether, collected by filtration and dried in vacuo to give ethyl (4-methyl-1H-indol-3-yl)-oxo-acetate (22.5 g). This compound was dissolved in tetrahydrofuran (250 mL) and subsequently added to lithium aluminium hydride (13 g, 0.35 mol) in tetrahydrofuran (500 mL). The resulting mixture was boiled under reflux for 1 h and then quenched with water (50 mL). The mixture was filtered, and the mother liquor was concentrated in vacuo. The residue was purified by flash chromatography (ethyl acetate/heptane 50:50) and subsequently crystallised from ethyl acetate to give 2-(4-methyl-1H-indol-3-yl)ethanol (14.4 g, 85%). To a mixture of 2-(4-methyl-1H-indol-3-yl)ethanol (14.4 g, 0.08 mol), borane trimethylamine complex (64 g, 0.88 mol) and 1,4-dioxane (500 mL) was added 37% aqueous HCl (55 mL), and the resulting mixture was stirred at room temperature for 16 h. The mixture was boiled under reflux for 1.5 h. 6 M aqueous HCl (260 mL) was added, and 300 mL of 1,4-dioxane/water was removed by distillation. The aqueous phase was cooled to 20° C. and then made alkaline by the use of 28% aqueous sodium hydroxide. The aqueous phase was added brine (500 mL) and extracted with ethyl acetate. The combined organic phase was washed with brine, dried ($MgSO_4$) and concentrated in vacuo. The residue was purified by flash chromatography (ethyl acetate) to give the title compound (12.5 g, 86%).

The following compound was prepared in a similar manner:

(RS)-2-(7-Methoxy-2,3-dihydro-1H-indol-3-yl)ethanol from 7-methoxy-1H-indole.

(S)-3-(2-Bromoethyl)-2,3-dihydro-1H-indole-1-carboxylic acid amide

To a solution of (S)-2-(2,3-dihydro-1H-indol-3-yl)ethanol (23.4 g, 0.14 mol), 37% HCl (aq) (15 mL) and water (15 mL) was added a solution of potassium cyanate (12.6 g, 0.15 mol) in water (85 mL) over a period of 10 min. The resulting mixture was added water (60 mL) and then poured onto a mixture of ice and brine. The aqueous phase was made alkaline by the use of 25% $NH_3$ (aq) and subsequently extracted with ethyl acetate. The combined organic phase was washed with brine and dried ($MgSO_4$). The organic phase was filtered and concentrated in vacuo (19.9 g). The residue was dissolved in tetrahydrofuran (400 mL) and triethylamine (20 mL), which subsequently was cooled to 3° C. To this mixture was added a solution of methanesulfonyl chloride (8.6 mL, 0.11 mol) in tetrahydrofuran (100 mL). The mixture was stirred at room temperature for 30 min, filtered and concentrated in vacuo. The crude product was dissolved in acetone (1400 mL) and lithium bromide (83.8 g, 0.96 mol) was added. The resulting mixture was boiled under reflux for 1 h, filtered and concentrated in vacuo. The residue was purified by flash chromatography (ethyl acetate) and precipitated from ethyl acetate and heptane to give the title compound (8.8 g).

The following compounds were prepared in a similar manner:

(R)-3-(2-Bromoethyl)-2,3-dihydro-1H-indole-1-carboxylic acid amide from (R)-2-(2,3-dihydro-1H-indol-3-yl)ethanol.

(R) or (S)-3-(2-Bromoethyl)-2,3-dihydro-5-fluoro-1H-indole-1-carboxylic acid amide from methyl (R) or (S)-(2,3-dihydro-5-fluoro-1H-indol-3-yl)acetate (enantiomer A) via (R) or (S)-2-(2,3-dihydro-5-fluoro-1H-indol-3-yl)ethanol.

(RS)-3-(2-Bromoethyl)-2,3-dihydro-1H-indole-1-carboxylic acid amide from (RS)-2-(2,3-dihydro-1H-indol-3-yl)ethanol.

1-[(S)-3-(2-Bromoethyl)-2,3-dihydro-1H-indol-1-yl]-ethanone

To a cooled (−28° C.) solution of (S)-2-(2,3-dihydro-1H-indol-3-yl)ethanol (8.5 g, 0.052 mol) in tetrahydrofuran (500 mL) and triethylamine (5.6 g, 0.055 mol) was added a solution of acetyl chloride (4.0 g, 0.051 mol) in tetrahydrofuran (200 mL) over a period of 35 min at −35 to −30° C. The mixture was stirred at −25 to −18° C. for 20 min, and an additional amount of triethylamine (6.3 g, 0.062 mol) was added followed by a solution of methanesulfonyl chloride (6 g, 0.052 mol) in tetrahydrofuran (200 mL) over a period of 25 min at −12 to −3° C. The resulting mixture was filtered and concentrated in vacuo. The residue was dissolved in acetone (600 mL) and lithium bromide (21.7 g, 0.25 mol) was added. The mixture was boiled under reflux for 1 h, filtered and concentrated in vacuo. The residue was purified by flash chromatography (heptane/ethyl acetate 1:1) to give the title compound (10.6 g, 76%).

The following compounds were prepared in a similar manner:

1-[(R)-3-(2-Bromoethyl)-2,3-dihydro-1H-indol-1-yl]-ethanone from (R)-2-(2,3-Dihydro-1H-indol-3-yl)ethanol.

1-[(R) or (S)-3-(2-Bromoethyl)-2,3-dihydro-5-fluoro-1H-indol-1-yl]-ethanone from methyl (R) or (S)-(2,3-dihydro-5-fluoro-1H-indol-3-yl)acetate (enantiomer A) via (R) or (S)-2-(2,3-dihydro-5-fluoro-1H-indol-3-yl)ethanol.

1-[(RS)-3-(2-Bromoethyl)-2,3-dihydro-1H-indol-1-yl]-ethanone from (RS)-2-(2,3-Dihydro-1H-indol-3-yl)ethanol.

1-[(RS)-3-(2-Bromoethyl)-4-methyl-2,3-dihydro-1H-indol-1-yl]-ethanone from (RS)-2-(4-Methyl-2,3-dihydro-1H-indol-3-yl)ethanol 1-[(RS)-3-(2-Bromoethyl)-7-methoxy-2,3-dihydro-1H-indol-1-yl]-ethanone from (RS)-2-(7-Methoxy-2,3-dihydro-1H-indol-3-yl)ethanol C. Indolines 5-{4-[(S)-2-(2,3-Dihydro-1H-indol-3-yl)-ethyl]-piperazin-1-yl}-1H-indole A mixture of 5-(piperazin-1-yl)-1H-indole (38.0 g, 0.19 mol), 1-[(S)-3-(2-bromoethyl)-2,3-dihydro-1H-indol-1-yl]-ethanone (49.6 g, 0.19 mol) and potassium carbonate (32 g, 0.23 mol) in a mixture of N,N-dimethyl formamide (400 mL) and butanone (800 mL) was boiled under reflux for 8 h. The mixture was filtered and concentrated in vacuo. The reaction was performed once more with the same amounts of starting material, and the combined residues were purified by flash chromatography (ethyl acetate/ethanol/triethylamine 90:5:5). The purified residue was precipitated from a mixture of methanol/ethyl acetate/heptane to give a solid (77.4 g). This compound (77.2 g, 0.20 mol) was suspended in methanol (1000 mL), and to this suspension was added a mixture of 37% HCl (aq) (125 mL) and water (125 mL). The resulting mixture was boiled under reflux for 4.5 h. The mixture was poured onto ice and brine, and the aqueous phase was made alkaline by the use of 25% $NH_3$ (aq). The aqueous phase was extracted with ethyl acetate, and the combined organic phase was washed with brine, dried ($MgSO_4$), filtered and concentrated in vacuo (75.1 g). The residue was purified by flash chromatography (ethyl acetate/ethanol/triethylamine 90:5:5) to give the title compound as a solid (58.8 g).

The following compounds were prepared in a similar manner:

5-{4-[(R)-2-(2,3-Dihydro-1H-indol-3-yl)-ethyl]-piperazin-1-yl}-1H-indole from 5-(piperazin-1-yl)-1H-indole and 1-[(R)-3-(2-bromoethyl)-2,3-dihydro-1H-indol-1-yl]-ethanone.

5-{4-[(R) or (S)-2-(2,3-Dihydro-5-fluoro-1H-indol-3-yl)-ethyl]-piperazin-1-yl}1-1H-indole from 5-(piperazin-1-yl)-1H-indole and 1-[(R) or (S)-3-(2-bromoethyl)-2,3-dihydro-5-fluoro-1H-indol-1-yl]-ethanone (obtained from enantiomer A).

5-{4-[(S)-2-(2,3-Dihydro-1H-indol-3-yl)-ethyl]-piperazin-1-yl}-1H-pyrrolo[2,3-c]pyridine from 5-(piperazin-1-yl)-1H-pyrrolo[2,3-c]pyridine and 1-[(S)-3-(2-bromoethyl)-2,3-dihydro-1H-indol-1-yl]-ethanone.

5-{4-[(RS)-2-(2,3-Dihydro-1H-indol-3-yl)-ethyl]-piperazin-1-yl}-1H-indole from 5-(piperazin-1-yl)-1H-indole and 1-[(RS)-3-(2-bromoethyl)-2,3-dihydro-1H-indol-1-yl]-ethanone.

5-{-4-[(S)-2-(2,3-Dihydro-1H-indol-3-yl)-ethyl]-piperazin-1-yl}-7-fluoro-1H-indole from 7-Fluoro-5-(piperazin-1-yl)-1H-indole and 1-[(S)-3-(2-bromoethyl)-2,3-dihydro-1H-indol-1-yl]-ethanone 5-{4-[2-((RS)-4-Methyl-2,3-dihydro-1H-indol-3-yl}-ethyl]-piperazin-1-yl)-1H-indole from 5-(piperazin-1-yl)-1H-indole and 1-[(RS)-3-(2-bromoethyl)-4-methyl-2,3-dihydro-1H-indol-1-yl]-ethanone 5-{4-[2-((RS)-7-Methoxy-2,3-dihydro-1H-indol-3-yl)-ethyl]-piperazin-1-yl}1H-indole from 5-(piperazin-1-yl)-1H-indole and 1-[(RS)-3-(2-bromoethyl)-7-methoxy-2,3-dihydro-1H-indol-1-yl]-ethanone.

5-{1-[(S)-2-(2,3-Dihydro-1H-indol-3-yl)-ethyl]-1,2,3,6-tetrahydropyridin-4-yl}1H-indole A mixture of 5-(pyridin-4-yl)-1H-indole (17.2 g, 0.089 mol), 1-[(S)-3-(2-bromoethyl)-2,3-dihydro-1H-indol-1-yl]-ethanone (28.5 g, 0.11 mol), 1,4-dioxane (900 mL), tetrahydrofuran (150 mL) and methanol (100 mL) was heated under reflux at approximately 80° C. for 68 h. The mixture was cooled, and the solid formed was collected by filtration and washed with tetrahydrofuran. The compound was dried in vacuo to give 1-[2-((S)-1-acetyl-2,3-dihydro-1H-indol-3-yl) ethyl]-4-(1H-indol-5-yl)pyridinium bromide (27.5 g, 64%), which was suspended in methanol (900 mL) and cooled (5° C.). To this mixture was added sodium borohydride (6.75 g, 0.18 mol) over a period of 20 min. The resulting mixture was stirred at 10° C. for 1 h and concentrated to about 200 mL. The mixture was poured onto a mixture of brine (750 mL) and 28% aqueous sodium hydroxide (20 mL), and the aqueous phase was extracted with a mixture of ethyl acetate and tetrahydrofuran. The combined organic phase was washed with brine, dried (MgSO$_4$), filtered and concentrated in vacuo. The residue was purified by flash chromatography (ethyl acetate/tetrahydrofuran/triethylamine 70:25:5) to give 1-((S)-3-{2-[4-(1H-indol-5-yl)-3,6-dihydro-2H-piperidin-1-yl]ethyl}-2,3-dihydro-1H-indol-1-yl)-ethanone (20.5 g, 85%). This compound (8.0 g, 0.02 mol) was dissolved in 1-propanol (220 mL) and heated to 60° C. To this mixture was added 28% aqueous sodium hydroxide, and the resulting mixture was boiled under reflux for 7 h. The mixture was cooled and poured onto brine. The aqueous phase was extracted with a mixture of ethyl acetate and tetrahydrofuran, and the combined organic phase was washed with brine, dried (MgSO$_4$), filtered and concentrated in vacuo. The residue was combined with a residue coming from another experiment starting from 1 g of 1-((S)-3-{2-[4-(1H-indol-5-yl)-3,6-dihydro-2H-piperidin-1-yl]ethyl}-2,3-dihydro-1H-indol-1-yl)-ethanone. The combined residue was purified by flash chromatography (ethyl acetate/triethylamine 95:5) to give the title compound (4.95 g).

5-{1-[(S)-2-(2,3-Dihydro-1H-indol-3-yl)-ethyl]-piperidin-4-yl}-1H-indole

A mixture of 1-((S)-3-{2-[4-(1H-indol-5-yl)-3,6-dihydro-2H-piperidin-1-yl]ethyl}-2,3-dihydro-1H-indol-1-yl)-ethanone (15.3 g, 0.040 mol), palladium (10 wt %, dry basis) on activated carbon (4.0 g), ammonium formate (50 g, 0.80 mol) and methanol (600 mL) was boiled under reflux for 3 h. The mixture was cooled and filtered, and the filter cake was washed with tetrahydrofuran. The organic phase was reduced in vacuo to 200 mL and poured onto a mixture of brine (1 L) and 28% aqueous sodium hydroxide (20 mL). The aqueous phase was extracted with ethyl acetate, and the combined organic phase was washed with brine, dried (MgSO$_4$) and concentrated in vacuo (13.2 g, 82%). This compound was dissolved in 1-propanol at 80° C., and 28% aqueous sodium hydroxide (100 mL) was added. The resulting mixture was boiled under reflux for 20 h. The mixture was poured onto brine, and the aqueous phase was extracted with ethyl acetate. The combined organic phase was washed with brine, dried (MgSO$_4$), filtered and concentrated in vacuo. The residue was purified by flash chromatography (ethyl acetate/triethylamine 95:5) to give the title compound (9.8 g, 80%).

Preparation of the Compounds of the Invention

EXAMPLES 1a, (+)-(S)-3-{2-[4-(1H-Indol-5-yl)-piperazin-1-yl]-ethyl}-2,3-dihydro-1H-indole-1-carboxylic acid amide

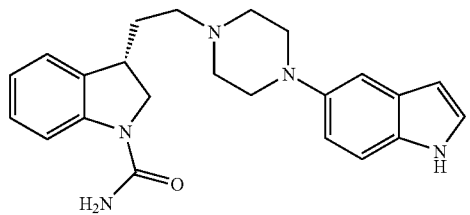

A mixture of 5-(piperazin-1-yl)-1H-indole (3.37 g, 0.017 mol), (S)-3-(2-bromoethyl)-2,3-dihydro-1H-indole-1-carboxylic acid amide (3.0 g, 0.11 mol), potassium carbonate (2.31 g, 0.017 mol) in butanone (450 mL) was boiled under reflux for 12 h. The mixture was filtered, concentrated in vacuo, and the residue was purified by flash chromatography (ethyl acetate/ethanol/triethylamine 70:25:5). The purified residue was precipitated from ethyl acetate to give the title compound as a white solid (3.0 g). Assignment of the optical rotation was done in dimethyl sulfoxide.

LC/MS (m/z) 390 (MH+); RT=1.55 (Method A).

The following compounds were prepared in a similar manner from:

1b, (+)-3-{2-[4-(1H-Indol-5-yl)-piperazin-1-yl]-ethyl}-2,3-dihydro-5-fluoro-1H-indole-1-carboxylic acid amide oxalate

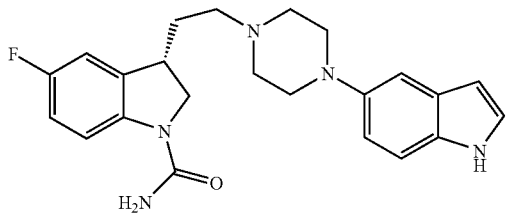

from 5-(piperazin-1-yl)-1H-indole and (R) or (S)-3-(2-bromoethyl)-2,3-dihydro-5-fluoro-1H-indole-1-carboxylic acid amide (obtained from enantiomer A). Assignment of the optical rotation was done in dimethyl sulfoxide.

LC/MS (m/z) 408 (MH+); RT=1.65 (Method A).

1c, (+)-(S)-3-{2-[4-(1H-Pyrrolo[2,3-c]pyridin-5-yl)-piperazin-1-yl]-ethyl}-2,3-dihydro-1H-indole-1-carboxylic acid amide

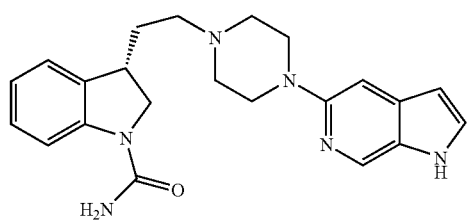

from 5-piperazin-1-yl-1H-pyrrolo[2,3-c]pyridine and (S)-3-(2-bromoethyl)-2,3-dihydro-1H-indole-1-carboxylic acid amide. Assignment of the optical rotation was done in dimethyl sulfoxide.

LC/MS (m/z) 391 (MH+); RT=1.05 (Method A).

1d, (+)-3-{2-[4-(1H-Pyrrolo[2,3-c]pyridin-5-yl)-piperazin-1-yl]-ethyl}-2,3-dihydro-5-fluoro-1H-indole-1-carboxylic acid amide

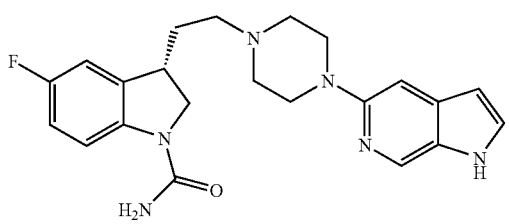

from 5-piperazin-1-yl-1H-pyrrolo[2,3-c]pyridine and (R) or (S)-3-(2-bromoethyl)-2,3-dihydro-5-fluoro-1H-indole-1-carboxylic acid amide (obtained from enantiomer A). Assignment of the optical rotation was done in dimethyl sulfoxide.

LC/MS (m/z) 409 (MH+); RT=1.23 (Method A).

1e, (RS)-3-{2-[4-(1H-Indol-5-yl)-piperazin-1-yl]-ethyl}-2,3-dihydro-1H-indole-1-carboxylic acid amide hydrochloride

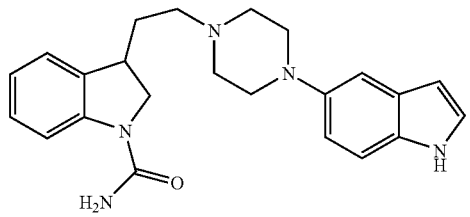

from 5-(piperazin-1-yl)-1H-indole and (RS)-3-(2-bromoethyl)-2,3-dihydro-1H-indole-1-carboxylic acid amide.

LC/MS (m/z) 390 (MH+); RT=1.56 (Method A).

2a, 2-((+)-(S)-3-{2-[4-(1H-Indol-5-yl)-piperazin-1-yl]-ethyl}-2,3-dihydro-1H-indol-1-yl)-acetamide dihydrochloride

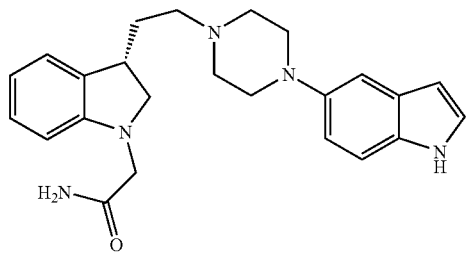

To a clear solution of 2-chloroacetamide (17.7 g, 0.19 mol) in N-methylpyrrolidin-2-one (500 mL) was slowly added a solution of 5-{4-[(S)-2-(2,3-dihydro-1H-indol-3-yl)-ethyl]-piperazin-1-yl}-1H-indole (52.6 g, 0.15 mol) in butanone (600 mL). Potassium iodide (29.0 g, 0.17 mol) and potassium carbonate (31.4 g, 0.15 mol) was added and the resulting mixture was boiled under reflux for 1 h, filtered and poured onto a mixture of ice and brine. The aqueous phase was extracted with ethyl acetate, and the combined organic phase was washed with brine, dried (MgSO4), filtered and concentrated in vacuo. The residue was purified by flash chromatography (ethyl acetate/ethanol/triethylamine 70:5:5) to give crude title compound (30.6 g). This was precipitated from methanol by addition of hydrochloric acid in diethyl ether until pH was approximately 3. The compound was collected by filtration as a powder (7.7 g). Assignment of the optical rotation was done in dimethyl sulfoxide.

LC/MS (m/z) 404 (MH+); RT=1.48 (Method A).

The following compounds were prepared in a similar manner.

2b, 2-((+)-3-{2-[4-(1H-Indol-5-yl)-piperazin-1-yl]-ethyl}-2,3-dihydro-5-fluoro-1H-indol-1-yl)-acetamide dihydrochloride

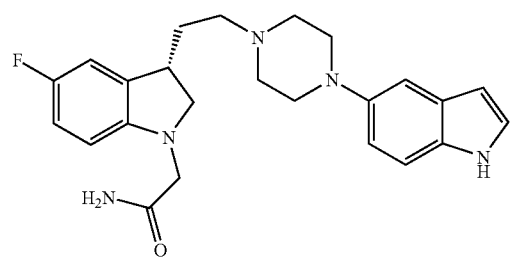

from 5-{4-[(R) or (S)-2-(2,3-dihydro-5-fluoro-1H-indol-3-yl)-ethyl]-piperazin-1-yl}-1H-indole (obtained from enantiomer A) and 2-chloroacetamide. Assignment of the optical rotation was done in dimethyl sulfoxide.

LC/MS (m/z) 422 (MH$^+$); RT=1.67 (Method A).

2c, 2-((+)-(S)-3-{2-[4-(1H-Pyrrolo[2,3-c]pyridin-5-yl)-piperazin-1-yl]-ethyl}-2,3-dihydro-1H-indol-1-yl)-acetamide dihydrochloride

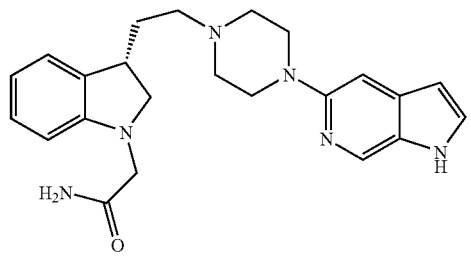

from 5-{4-[(S)-2-(2,3-dihydro-1H-indol-3-yl)-ethyl]-piperazin-1-yl}-1H-pyrrolo[2,3-c]pyridine and 2-chloroacetamide. Assignment of the optical rotation was done in dimethyl sulfoxide.

LC/MS (m/z) 405 (MH$^+$); RT=1.16 (Method A).

2d, 2-((−)-(R)-3-{2-[4-(1H-Indol-5-yl)-piperazin-1-yl]-ethyl}-2,3-dihydro-1H-indol-1-yl)-acetamide dihydrochloride

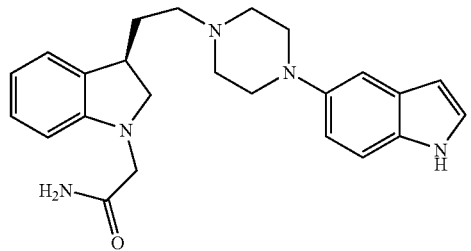

from 5-{4-[(R)-2-(2,3-dihydro-1H-indol-3-yl)-ethyl]-piperazin-1-yl}-1H-indole and 2-chloroacetamide. Assignment of the optical rotation was done in dimethyl sulfoxide.

LC/MS (m/z) 404 (MH$^+$); RT=1.51 (Method A).

2e, 2-((RS)-3-{2-[4-(1H-Indol-5-yl)-piperazin-1-yl]-ethyl}-2,3-dihydro-1H-indol-1-yl)-acetamide oxalate

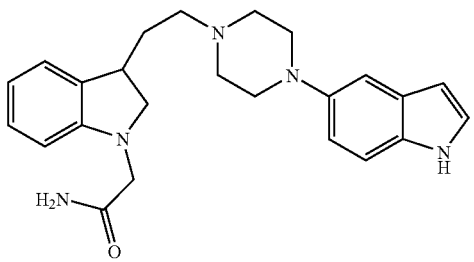

from 5-{4-[(RS)-2-(2,3-dihydro-1H-indol-3-yl)-ethyl]-piperazin-1-yl}-1H-indole and 2-chloroacetamide.

LC/MS (m/z) 404 (MH$^+$); RT=1.0 (Method B).

2f, 2-((+)-(S)-3-{2-[4-(7-Fluoro-1H-indol-5-yl)-piperazin-1-yl]-ethyl}-2,3-dihydro-1H-indol-1-yl)-acetamide oxalate.

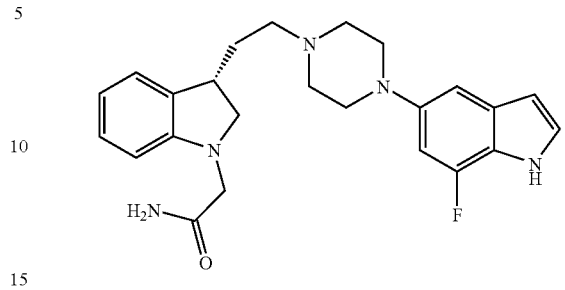

from 5-{4-[(S)-2-(2,3-dihydro-1H-indol-3-yl)-ethyl]-piperazin-1-yl}-7-fluoro-1H-indole and 2-chloroacetamide. Assignment of the optical rotation was done in dimethyl sulfoxide.

LC/MS (m/z) 422 (MH+); RT=1.1 (Method B).

2g, 2-((RS)-3-{2-[4-(1H-Indol-5-yl)-piperazin-1-yl]-ethyl}-4-methyl-2,3-dihydro-1H-indol-1-yl)-acetamide oxalate

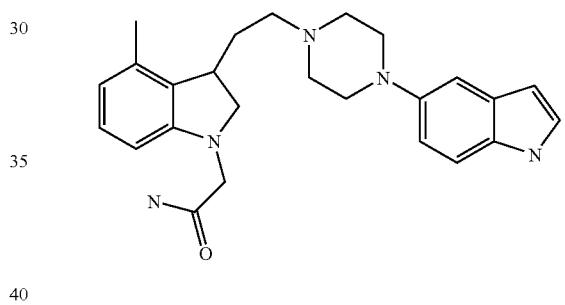

from 5-{4-[2-((RS)-4-methyl-2,3-dihydro-1H-indol-3-yl)-ethyl]-piperazin-1-yl}-1H-indole and 2-chloroacetamide.

LC/MS (m/z) 418 (MH+); RT=0.40 (Method C).

2h, 2-((RS)-3-{2-[4-(1H-Indol-5-yl)-piperazin-1-yl]-ethyl}-7-methoxy-2,3-dihydro-1H-indol-1-yl)-acetamide oxalate

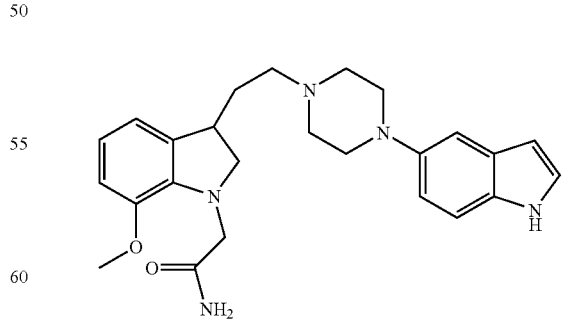

from 5-{4-[2-((RS)-7-methoxy-2,3-dihydro-1H-indol-3-yl)-ethyl]-piperazin-1-yl}-1H-indole and 2-chloroacetamide.

LC/MS (m/z) 434 (MH$^+$); RT=0.37 (Method C).

2i, 2-((+)-(S)-3-{2-[4-(1H-Indol-5-yl)-piperazin-1-yl]-ethyl}-2,3-dihydro-1H-indol-1-yl)-N-methyl-acetamide oxalate

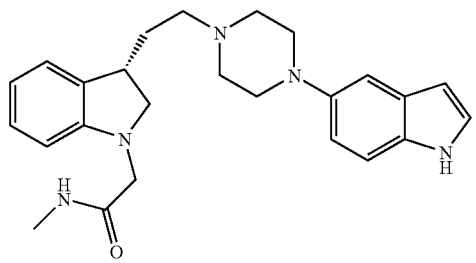

from 5-{4-[(S)-2-(2,3-dihydro-1H-indol-3-yl)-ethyl]-piperazin-1-yl}-1H-indole and 2-chloro-N-methylacetamide. Assignment of the optical rotation was done in dimethyl sulfoxide.

LC/MS (m/z) 418 (MH$^+$); RT=1.07 (Method B).

2j, N-Methyl-2-((+)-(S)-3-{2-[4-(1H-pyrrolo[2,3-c]pyridin-5-yl)-piperazin-1-yl]-ethyl}-2,3-dihydro-1H-indol-1-yl)-acetamide oxalate

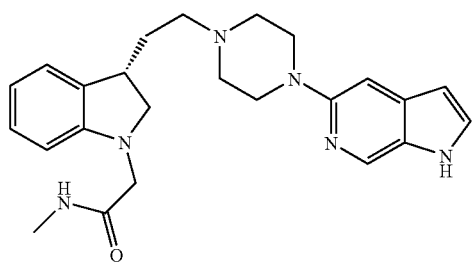

from 5-{4-[(S)-2-(2,3-dihydro-1H-indol-3-yl)-ethyl]-piperazin-1-yl}-1H-pyrrolo[2,3-c]pyridine and 2-chloro-N-methyl-acetamide. Assignment of the optical rotation was done in dimethyl sulfoxide.

LC/MS (m/z) 419 (MH$^+$); RT=0.78 (Method B).

2k, (RS)-2-((S)-3-{2-[4-(1H-Indol-5-yl)-piperazin-1-yl]-ethyl}-2,3-dihydro-1H-indol-1-yl)-propionamide oxalate

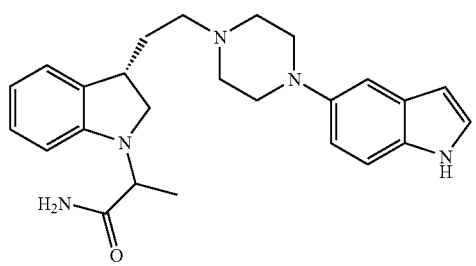

from 5-{4-[(S)-2-(2,3-dihydro-1H-indol-3-yl)-ethyl]-piperazin-1-yl}-1H-indole and 2-chloropropionamide. The compound is approximately a 1.1 mixture of diastereomers according to NMR.

LC/MS (m/z) 418 (MH$^+$); RT=1.03 (Method B).

2l, 2-((+)-(S)-3-{2-[4-(1H-Indol-5-yl)-piperazin-1-yl]-ethyl}-2,3-dihydro-1H-indol-1-yl)-N,N-dimethyl-acetamide oxalate

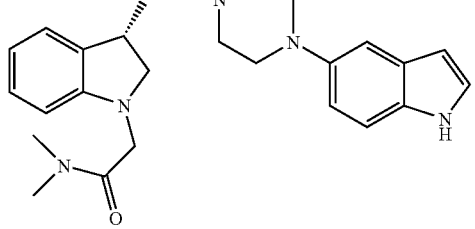

from 5-{4-[(S)-2-(2,3-dihydro-1H-indol-3-yl)-ethyl]-piperazin-1-yl}-1H-indole and 2-chloro-N,N-dimethylacetamide. Assignment of the optical rotation was done in dimethyl sulfoxide.

LC/MS (m/z) 432 (MH+); RT=0.41 (Method C).

2m, 2-((+)-(S)-3-{2-[4-(1H-Indol-5-yl)-3,6-dihydro-2H-piperidin-1-yl]-ethyl}-2,3-dihydro-1H-indol-1-yl)-acetamide oxalate

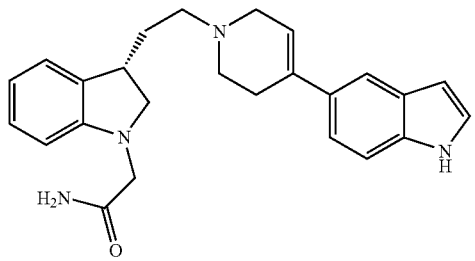

from 5-{1-[(S)-2-(2,3-dihydro-1H-indol-3-yl)-ethyl]-1,2,3,6-tetrahydropyridin-4-yl}-1H-indole and 2-chloroacetamide. Assignment of the optical rotation was done in dimethyl sulfoxide.

LC/MS (m/z) 401 (MH$^+$); RT=1.12 (Method B).

2n, 2-((+)-(S)-3-{2-[4-(1H-Indol-5-yl)-piperidin-1-yl]-ethyl}-2,3-dihydro-1H-indol-1-yl)-acetamide oxalate

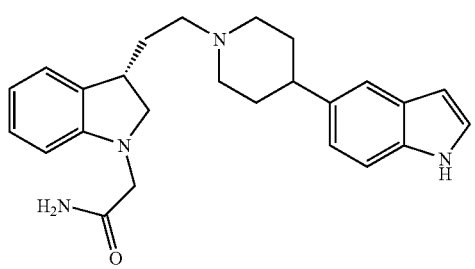

from 5-{1-[(S)-2-(2,3-dihydro-1H-indol-3-yl)-ethyl]-piperidin-4-yl}-1H-indole and 2-chloroacetamide. Assignment of the optical rotation was done in dimethyl sulfoxide.

LC/MS (m/z) 403 (MH+); RT=0.4 (Method C).

3a, 2-((+)-(S)-3-{2-[4-(1H-Indol-5-yl)-piperazin-1-yl]-ethyl}2,3-dihydro-1H-indol-1-yl)-2-oxo-acetamide

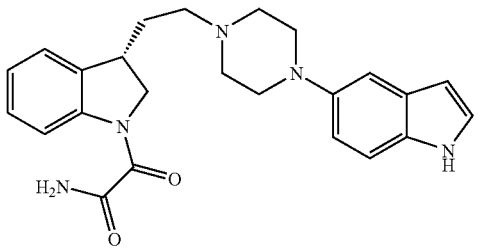

To a solution of oxalamic acid (2.35 g, 0.026 mol) and 1,1'-carbonyldiimidazole (4.66 g, 0.029 mol) in dry N,N-dimethyl formamide (50 mL) was slowly added a solution of 5-{4-[(S)-2-(2,3-dihydro-1H-indol-3-yl)-ethyl]-piperazin-1-yl}-1H-indole (8.3 g, 0.024 mol) in N,N-dimethyl formamide (75 mL). The resulting mixture was stirred at room temperature for 1 h, filtered and poured onto brine. The aqueous phase was extracted with ethyl acetate, and the combined organic phase was washed with brine, dried (MgSO$_4$), filtered and concentrated in vacuo. The residue was purified by flash chromatography (ethyl acetate/heptane/triethylamine 70:25:5) to give the title compound as an oil (6.5 g). The oil was precipitated from ethyl acetate to give a powder (4.1 g). Assignment of the optical rotation was done in dimethyl sulfoxide.

LC/MS (m/z) 418 (MH$^+$); RT=1.62 (Method A).

The following compound was prepared in a similar manner:

3b, 2-Oxo-2-((+)-(S)-3-{2-[4-(1H-pyrrolo[2,3-c]pyridin-5-yl)-piperazin-1-yl]-ethyl}-2,3-dihydro-1H-indol-1-yl)-acetamide

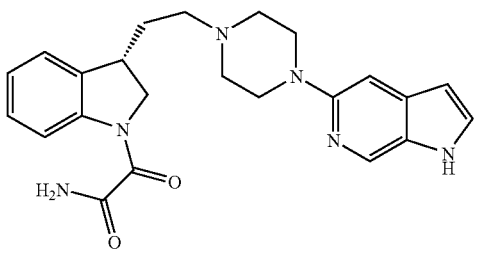

from 5-{4-[(S)-2-(2,3-dihydro-1H-indol-3-yl)-ethyl]-piperazin-1-yl}-1H-pyrrolo[2,3-c]pyridine. Assignment of the optical rotation was done in dimethyl sulfoxide.

LC/MS (m/z) 419 (MH$^+$); RT=1.16 (Method A).

3c, 2-((+)-(S)-3-{2-[4-(1H-Indol-5-yl)-piperidin 1-yl]-ethyl}-2,3-dihydro-1H-indol-1-yl)-2-oxoacetamide oxalate

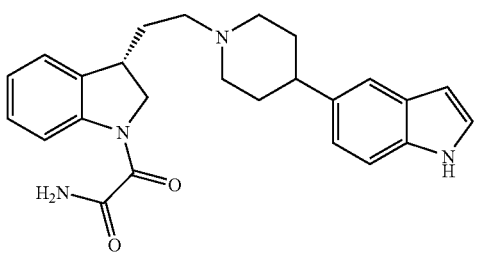

from 5-{1-[(S)-2-(2,3-dihydro-1H-indol-3-yl)-ethyl]-piperidin-4-yl}-1H-indole and oxalamic acid. Assignment of the optical rotation was done in dimethyl sulfoxide.

LC/MS (m/z) 417 (MH$^+$); RT=0.39 (Method C).

3d, 2-((RS)-3-{2-[4-(1H-Indol-5-yl)-piperazin-1-yl]-ethyl}-7-methoxy-2,3-dihydro-1H-indol-1-yl)-2-oxo-acetamide oxalate

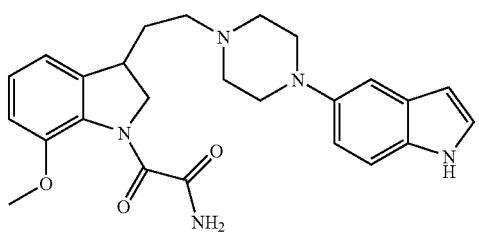

from 5-{4-[2-((RS)-7-methoxy-2,3-dihydro-1H-indol-3-yl)-ethyl]-piperazin-1-yl}-1H-indole and oxalamic acid.

LC/MS (m/z) 448 (MH$^+$); RT=0.3 (Method C).

4a, (+)-(S)-3-{2-[4-(1H-Indol-5-yl)-3,6-dihydro-2H-piperidin-1-yl]-ethyl}-2,3-dihydro-1H-indole-1-carboxylic acid amide hydrochloride

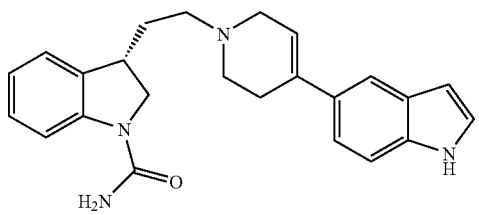

A mixture of 5-(pyridin-4-yl)-1H-indole (2.6 g, 0.13 mol), 1,4-dioxane (250 mL), tetrahydrofuran (20 mL) and methanol (10 mL) was heated to reflux temperature, and (S)-3-(2-bromoethyl)-2,3-dihydro-1H-indole-1-carboxylic acid amide (3.9 g, 0.015 mol) was added. The resulting mixture was boiled under reflux for 96 h. The mixture was cooled, and the liquid decanted off. The residue was washed with ethyl acetate and then dissolved in methanol (500 mL) under heating. The organic phase was concentrated in vacuo to give 1-[2-((S)-1-carbamoyl-2,3-dihydro-1H-indol-3-yl)ethyl]-4-(1H-indol-5-yl)pyridinium bromide (5.7 g, 75%). This compound was suspended in methanol (130 mL), and sodium borohydride (1.48 g, 0.039 mol) was added over a period of 10 min at 12-20° C. The resulting mixture is stirred at 10° C. for 30 min and then poured onto a mixture of brine (500 mL) and 28% aqueous sodium hydroxide (50 mL). The aqueous phase was extracted with ethyl acetate, and the combined organic phase was washed with brine, dried (MgSO$_4$), filtered and concentrated in vacuo. The residue was purified by flash chromatography (ethyl acetate/ethanol/triethylamine 85:10:5) to give crude title compound (3.5 g). Starting from 0.7 g of crude compound, the hydrochloric acid salt was prepared (0.63 g). Assignment of the optical rotation was done in dimethyl sulfoxide.

LC/MS (m/z) 387 (MH$^+$); RT=1.11 (Method B).

5a, (+)-(S)-3-{2-[4-(1H-Indol-5-yl)-piperidin-1-yl]-ethyl}-2,3-dihydro-1H-indole-1-carboxylic acid amide oxalate

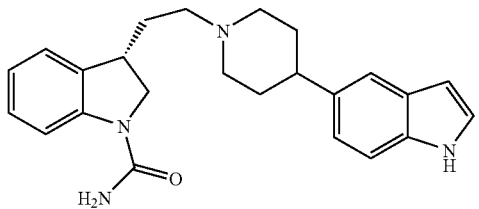

A mixture of (S)-3-{2-[4-(1H-indol-5-yl)-3,6-dihydro-2H-piperidin-1-yl]-ethyl}-2,3-dihydro-1H-indole-1-carboxylic acid amide (2.6 g, 0.007 mol), palladium (10 wt %, dry basis) on activated carbon (1.0 g), ammonium formate (8.5 g, 0.13 mol) and methanol (130 mL) was boiled under reflux for 6 h. The mixture was cooled and filtered, and the filter cake was washed with ethanol. The organic phase was poured onto a mixture of brine (500 mL) and 28% aqueous sodium hydroxide (10 mL). The aqueous phase was extracted with ethyl acetate, and the combined organic phase was washed with brine, dried ($MgSO_4$) and concentrated in vacuo. The residue was purified by flash chromatography (ethyl acetate/ethanol/triethylamine 85:10:5) to give the title compound, which was precipitated as the oxalate salt (2.3 g). Assignment of the optical rotation was done in dimethyl sulfoxide.

LC/MS (m/z) 389 ($MH^+$); RT=1.09 (Method B).

List of reagents

| Name | Supplier | CAS No. | Cat.No. |
|---|---|---|---|
| Acetyl Chloride | FLUKA | 75-36-5 | 01000 |
| Lithium Bromide | ALDRICH | 7550-35-8 | 21,322-5 |
| Methanesulfonyl Chloride | ALDRICH | 124-63-0 | 47,125-9 |
| Lithium Aluminium Hydride | ALDRICH | 16853-85-3 | 19,987-7 |
| Sodium Cyanoborohydride | ALDRICH | 25895-60-7 | 15,615-9 |
| 5-Nitro-1H-indole | ALDRICH | 6146-52-7 | N1,760-2 |
| (1H-Indole-3-yl)acetic Acid | AVOCADO | 87-51-4 | 10556 |
| Ammonium Formate | ALDRICH | 540-69-2 | 15,626-4 |
| Triethylamine | RIEDEL-DEHAËN | 121-44-8 | 16304 |
| Potassium Iodide | ALDRICH | 7681-11-0 | 22,194-5 |
| 1,1'-Carbonyldiimidazole | ALDRICH | 530-62-1 | 11,553-3 |
| Ethyl Piperazine-1-carboxylate | ACROS ORGANICS | 120-43-4 | 11887-1000 |
| N,N-Dimethylformamide Dimethyl Acetal | LANCASTER | 4637-24-5 | 0621 |
| Oxalamic Acid | ALDRICH | 471-47-6 | 0-920-4 |
| Di-tert-Butyl Dicarbonate | FLUKA | 24424-99-5 | 34660 |
| Potassium Cyanate | MERCK SCHUCHARDT | 590-28-3 | 804957 |
| N,N-Dimethyl Formamide | FLUKA | 68-12-2 | 40255 |
| Methanol | FLUKA | 67-56-1 | 65550 |
| 2-Butanone | ACROS ORGANICS | 78-93-3 | 149670010 |
| Tetrahydrofuran | RIEDEL-DEHAËN | 109-99-9 | 16212 |
| 2-Propanol | RIEDEL-DEHAËN | 67-63-0 | 24137 |
| Sodium Hydrogencarbonate | ALDRICH | 144-55-8 | 34,094-4 |
| Potassium Hydroxide | ALDRICH | 1310-58-3 | 22,147-3 |
| Phosphoric Acid (85% in water) | RIEDEL-DEHAËN | 7664-38-2 | 04107 |
| Methanesulfonic Acid (70% in water) | ALDRICH | 75-75-2 | 47,134-8 |
| Sodium DihydrogenPhosphate Monohydrate | ALDRICH | 10049-21-5 | 22,352-2 |
| Sodium Hydroxide | ACROS ORGANICS | 1310-73-2 | 134070025 |
| Sodium Chloride | ACROS ORGANICS | 7647-14-5 | 20779-0050 |
| Potassium Carbonate | AVOCADO | 584-08-7 | 16625 |
| Diethyl Ether | RIEDEL-DEHAËN | 60-29-7 | 24004 |
| 1,4-Dioxane | SIGMA-ALDRICH | 123-91-1 | 360481-2L |
| Di-isopropyl Ether | RIEDEL-DEHAËN | 108-20-3 | 33159 |
| 2-Chloro-5-nitro-4-picoline | ACROS ORGANICS | 23056-33-9 | 361030000 |
| Ammonia (25% in water) | MERCK | 7664-41-7 | 5432 |
| Hydrochloric Acid (37% in water) | ALDRICH | 7647-01-0 | 32,033-1 |
| Sulfuric Acid (95-98% in water) | ALDRICH | 7664-93-9 | 43,558-9 |
| Acetic Acid | ALDRICH | 64-19-7 | 24,285-3 |
| Ethyl Acetate | ALDRICH | 141-78-6 | 31,990-2 |
| Heptane | ALDRICH | 142-82-5 | H219-8 |

-continued

| List of reagents | | | |
|---|---|---|---|
| Name | Supplier | CAS No. | Cat.No. |
| Ethanol | ALDRICH | 64-17-5 | 45,984-4 |
| Acetone | ALDRICH | 67-64-1 | 17,912-4 |
| Dichloromethane | ALDRICH | 75-09-2 | D6,510-0 |
| Hydrogen Chloride (2.0M in diethylether) | ALDRICH | 7647-01-0 | 45,518-0 |
| Oxalic Acid | ALDRICH | 144-62-7 | 24,117-2 |
| N-Methylpyrrolidin-2-one | RIEDEL-DEHAËN | 872-50-4 | 15780 |
| Hydrogen | ALDRICH | 1333-74-0 | 29,539-6 |
| Novozyme 435 | ALDRICH | — | 53,732-2 |
| Magnesium Sulfate | ALDRICH | 7487-88-9 | 20,809-4 |
| Palladium, 5 wt % (dry basis) on activated carbon | ALDRICH | — | 33,011-6 |
| Palladium, 10 wt % (dry basis) on activated carbon | ALDRICH | 7440-05-3 | 20,569-9 |
| Silica gel, Merck grade 9385 | ALDRICH | 112926-00-8 | 22,719-6 |
| Molecular sieves 3A | ALDRICH | — | 20,858-2 |
| Filter agent, Celite 521 | ALDRICH | 61790-53-2 | 22,179-1 |
| Activated carbon | ALDRICH | 7440-44-0 | 16,155-1 |
| Di-sodium Hydrogen Phosphate, Dodecahydrate | ACROS ORGANICS | 10039-32-4 | 27106-0025 |
| N-Benzyliminodiacetic acid | ALDRICH | 3987-53-9 | B2,475-8 |
| Platinum Oxide | ALDRICH | 1314-15-4 | 52,061-6 |
| Borane Trimethylamine Complex | ALDRICH | 75-22-9 | 17,898-5 |
| 1-Propanol | RIEDEL-DEHAËN | 71-23-8 | 24135 |
| 2-Chloroacetamide | ALDRICH | 79-07-2 | 10,802-2 |
| 2-Chloro-N,N-dimethylacetamide | FLUKA | 2675-89-0 | 24350 |
| 2-Chloro-N-methylacetamide | ABCR | 96-30-0 | FR-1355 |
| 2-Chloropropionamide | ALDRICH | 27816-36-0 | 19,239-2 |
| Pyridin-4-boronic acid | ALDRICH | 1692-15-5 | 63,449-2 |
| tert-Butyl 5-Bromoindole-1-carboxylate | ALDRICH | 182344-70-3 | 55,7749 |
| Sodium Carbonate | ALDRICH | 497-19-8 | 22,353-0 |
| Tetrakis(triphenylphosphine)palladium (0) | ALDRICH | 14221-01-3 | 21,666-6 |
| Toluene | RIEDEL-DEHAËN | 108-88-3 | 24526 |
| 7-Fluoro-1H-indole | APOLLO | 387-44-0 | PC9454 |
| 7-Methoxy-1H-indole | ALDRICH | 3189-22-8 | 11,398-0 |
| Oxalyl Chloride | ALDRICH | 79-37-8 | 22,101-5 |
| 4-Methyl-1H-indole | ALDRICH | 16096-32-5 | 24,630-1 |
| Sodium borohydride | ALDRICH | 16940-66-2 | 48,088-6 |
| p-Xylene | ALDRICH | 106-42-3 | 31,719-5 |
| 100% Nitric acid | MERCK | 7697-37-2 | 1.00450.1000 |

Pharmacological Testing

The compounds of the invention were characterised in vitro in dopamine $D_4$, serotonin 5-$HT_{2A}$ and microsomal stability assays according to the following methods:

$^3$[H]-YM-09151-2 Binding to Dopamine $D_4$ Receptors

CHO cells expressing human recombinant $D_{4.2}$ receptors were generated at Lundbeck using standard stable transfection techniques. Membranes were harvested using standard protocols and affinities were measured by the addition of a serial dilution of compound to a membrane preparation in a mixture of 50 mM Tris-HCl, 5 mM $Na_2$-EDTA Titriplex III, 5 mM $MgCl_2$, 5 mM KCl and 1.5 mM $CaCl_2$ 0.06 nM $^3$[H]-YM-09151-2 was used as the radioligand assessing the affinity for the human $D_{4.2}$ receptor. Total binding was determined in the presence of buffer and non-specific binding was determined in the presence of 10 μM Clozapine. The mixture was incubated for 30 minutes at 37° C., cooled briefly on ice. Bound and free radioactivity was separated by vacuum filtration on GF/C filters pretreated with 0,1% Polyetyleneimine (PEI) and filters were counted in a scintillation counter.

Dopamine $D_4$ Efficacy as Determined by a cAMP Assay

The ability of the compounds to inhibit the $D_{4.2}$ receptor mediated inhibition of cAMP formation in CHO cells stably expressing the human recombinant $D_{4.2}$ receptor was measure as follows.

Cells were seeded in 96 well plates with 400 cells/well 4 days prior to the experiment. On the day of the experiment the cells were washed once in preheated G buffer (1 mM $MgCl_2$, 0.9 mM $CaCl_2$, 1 mM IBMX in PBS) and the assay was initiated by addition of 100 μl of a mixture of 1 μM quinpirole, 10 μM forskolin and test compound in G buffer. The cells were incubated 20 minutes at 37° C. and the reaction was stopped by the addition of 100 μl S buffer (0.1 M HCl and 0.1 mM $CaCl_2$) and the plates were placed at 4° C. for 1 h. 68 μl N buffer (0.15 M NaOH and 60 mM NaAc) were added and the plates were shaken for 10 minutes. 60 μl of the reaction were transferred to cAMP FlashPlates (DuPont NEN) containing 40 μl 60 mM NaAc pH 6.2 and 100 μl IC mix (50 mM NaAc pH 6.2, 0.1% NaAzid, 12 mM $CaCl_2$, 1% BSA and 0.15 μCi/ml $^{125}$I-cAMP) were added. Following an 18-h incubation at 4° C. the plates were washed once and counted in a Wallac TriLux counter.

Serotonin 5-HT$_{2A}$ Efficacy as Determined by a Ca$^{2+}$-release Assay 2 or 3 days before the experiment, CHO cells expressing 250 fmol/mg 5-HT$_{2A}$ receptors are plated at a density sufficient to yield a mono-confluent layer on the day of the experiment. The cells are dye loaded (Ca$^{2+}$-kit from Molecular Devices and using Hank's balanced salt w/o phenol red, added 20 mM HEPES and pH adjusted to 7.4 with 2M NaOH as assay buffer) for 60 minutes at 37° C. in a 5% CO$_2$ incubator at 95% humidity. Lacer intensity is set to a suitable level to obtain basal values of approximately 8000-10000 fluorescence units. The variation in basal fluorescence should be less than 10%. EC$_{50}$ values are assessed using increasing concentrations of test compound covering at least 3 decades. IC$_{50}$ values are assessed challenging the same range of concentrations of test substances with EC$_{85}$ of 5-HT. Test substances are added to the cells 5 minutes before the 5-HT. K$_i$ values were calculated using Cheng-Prusoff equation. % Stimulation of a concentration of the test compound is measured with respect to a maximal concentration of 5-HT (100%). % Inhibition of a concentration of the test compound is measured as the percentage with which the response of EC$_{85}$ of 5-HT is lowered. Maximum inhibition is the level of inhibition the curve reaches.

In Vitro Stability in Human and Rat Liver Microsomes

The stability of compounds in liver microsomes is determined by the T½ method, i.e. the disappearance of 1 µM drug is measured over time by LCMS. 0.5 mg/ml of microsomal protein (liver microsomes from several donors pooled to obtain an average enzyme content) is used in a NADPH (Nicotinamide-Adenine Dinucleotide Phosphate, reduced form) generating system (1.3 mM NADP (oxidized form), 3.3 mM glucose 6-phosphate and 0.4 U/ml glucose 6-phosphate dehydrogenase), 3.3 mM MgCl2 (magnesium Chloride), 0.1 M Potassium phosphate buffer (pH 7.4), in a total volume of 100 µl, and stopping the incubations at time points 0, 5, 15, 30 and 60 min with 1:1 v/v acetonitrile. The half live is subsequently scaled to the metabolic competence of a whole liver using 45 mg microsome/g liver, 45 g and 20 g liver/kg and Std. weight 70 kg and 0.25 kg, human and rats respectively.

What is claimed is:

1. A compound of formula I

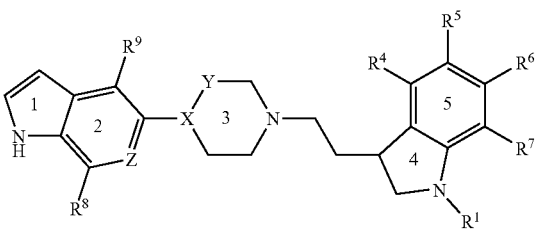

wherein X—Y is N—CH$_2$;
Z is CR$^{10}$ or N;
R$^1$ is A, A' or A"

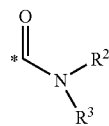

-continued

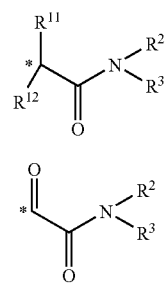

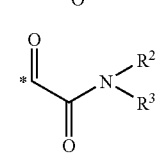

wherein * indicates the atom attached to N via a bond;
R$^2$ and R$^3$ are independently selected from hydrogen and C$_{1-6}$-alkyl;
R$^4$-R$^7$ are independently selected from hydrogen, C$_{1-6}$-alkyl, C$_{1-6}$-alkoxy and halogen;
R$^8$ and R$^9$ are independently selected from hydrogen and halogen;
R$^{10}$ is hydrogen or halogen;
R$^{11}$ and R$^{12}$ are independently selected from hydrogen and C$_{1-6}$-alkyl;
or enantiomers or pharmaceutically acceptable salts thereof.

2. A compound according to claim 1 wherein Z is CR$^{10}$.
3. A compound according to claim 1 wherein Z is N.
4. A compound according to claim 1 wherein R$^1$ is A

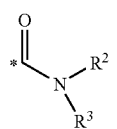

wherein * indicates the atom attached to N via a bond.
5. A compound according to claim 1 wherein R$^1$ is A'

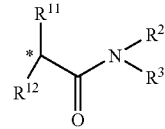

wherein * indicates the atom attached to N via a bond.
6. A compound according to claim 1 wherein R$^1$ is A"

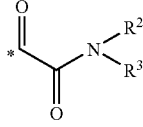

wherein * indicates the atom attached to N via a bond.
7. A compound according to claim 1, wherein R$^2$ and R$^3$ are independently selected from hydrogen and methyl.
8. A compound according to claim 1 wherein both R$^2$ and R$^3$ are hydrogen.
9. A compound according to claim 1 wherein R$^4$-R$^7$ are independently selected from hydrogen, methyl, methoxy and fluoro.
10. A compound according to claim 9, wherein only one of R$^4$-R$^7$ selected from R$^4$, R$^5$ and R$^7$ is different from hydrogen.
11. A compound according to claim 1 wherein R$^4$-R$^7$ are all hydrogen.

12. A compound according to claim 1 wherein $R^8$ and $R^9$ are independently selected from hydrogen and fluoro.

13. A compound according to claim 12 wherein both $R^8$ and $R^9$ are hydrogen.

14. A compound according to claim 1 wherein $R^{10}$ is hydrogen or fluoro.

15. A compound according to claim 14 wherein $R^{10}$ is hydrogen.

16. A compound according to claim 1 wherein $R^{11}$ and $R^{12}$ are independently selected from hydrogen, methyl and ethyl.

17. A compound according to claim 16 wherein both $R^{11}$ and $R^{12}$ are hydrogen.

18. A compound according to claim 1, wherein $R^2$ and $R^3$ are both hydrogen; $R^4$, $R^5$, $R^6$ and $R^7$ are selected from hydrogen, methyl, fluoro and methoxy;
$R^8$, $R^9$, $R^{10}$, $R^{11}$ and $R^{12}$ are hydrogen.

19. A compound according to claim 18, wherein Z is $CR^{10}$.

20. A compound selected from the group consisting of:
(+)-(S)-3-{2-[4-(1H-Indol-5-yl)-piperazin-1-yl]-ethyl}-2,3-dihydro-1H-indole-1-carboxylic acid amide;
(+)-3-{2-[4-(1H-Indol-5-yl)-piperazin-1-yl]-ethyl}-2,3-dihydro-5-fluoro-1H-indole-1-carboxylic acid amide;
(+)-(S)-3-{2-[4-(1H-Pyrrolo[2,3-c]pyridin-5-yl)-piperazin-1-yl]-ethyl}-2,3-dihydro-1H-indole-1-carboxylic acid amide;
(+)-3-{2-[4-(1H-Pyrrolo[2,3-c]pyridin-5-yl)-piperazin-1-yl]-ethyl}-2,3-dihydro-5-fluoro-1H-indole-1-carboxylic acid amide;
(RS)-3-{2-[4-(1H-Indol-5-yl)-piperazin-1-yl]-ethyl}-2,3-dihydro-1H-indole-1-carboxylic acid amide;
2-((+)-(S)-3-{2-[4-(1H-Indol-5-yl)-piperazin-1-yl]-ethyl}-2,3-dihydro-1H-indol-1-yl)-acetamide;
2-((+)-3-{2-[4-(1H-Indol-5-yl)-piperazin-1-yl]-ethyl}-2,3-dihydro-5-fluoro-1H-indol-1-yl)-acetamide;
2-((+)-(S)-3-{2-[4-(1H-Pyrrolo[2,3-c]pyridin-5-yl)-piperazin-1-yl]-ethyl}-2,3-dihydro-1H-indol-1-yl)-acetamide;
2-((−)-(R)-3-{2-[4-(1H-Indol-5-yl)-piperazin-1-yl]-ethyl}-2,3-dihydro-1H-indol-1-yl)-acetamide;
2-((RS)-3-{2-[4-(1H-Indol-5-yl)-piperazin-1-yl]-ethyl}-2,3-dihydro-1H-indol-1-yl)-acetamide;
2-((+)-(S)-3-{2-[4-(7-Fluoro-1H-indol-5-yl)-piperazin-1-yl]-ethyl}-2,3-dihydro-1H-indol-1-yl)-acetamide;
2-((RS)-3-{2-[4-(1H-Indol-5-yl)-piperazin-1-yl]-ethyl}-4-methyl-2,3-dihydro-1H-indol-1-yl)-acetamide;
2-((RS)-3-{2-[4-(1H-Indol-5-yl)-piperazin-1-yl]-ethyl}-7-methoxy-2,3-dihydro-1H-indol-1-yl)-acetamide;
2-((+)-(S)-3-{2-[4-(1H-Indol-5-yl)-piperazin-1-yl]-ethyl}-2,3-dihydro-1H-indol-1-yl)-N-methyl-acetamide;
N-Methyl-2-((+)-(S)-3-{2-[4-(1H-pyrrolo[2,3-c]pyridin-5-yl)-piperazin-1-yl]-ethyl}-2,3-dihydro-1H-indol-1-yl)-acetamide;
(RS)-2-((S)-3-{2-[4-(1H-Indol-5-yl)-piperazin-1-yl]-ethyl}-2,3-dihydro-1H-indol-1-yl)-propionamide;
2-((+)-(S)-3-{2-[4-(1H-Indol-5-yl)-piperazin-1-yl]-ethyl}-2,3-dihydro-1H-indol-1-yl)-N,N-dimethyl-acetamide;
2-((+)-(S)-3-{2-[4-(1H-Indol-5-yl)-piperazin-1-yl]-ethyl}-2,3-dihydro-1H-indol-1-yl)-2-oxo-acetamide;
2-Oxo-2-((+)-(S)-3-{2-[4-(1H-pyrrolo [2,3-c]pyridin-5-yl)-piperazin-1-yl]-ethyl}-2,3-dihydro-1H-indol-1-yl)-acetamide; and
2-((RS)-3-{2-[4-(1H-Indol-5-yl)-piperazin-1-yl]-ethyl}-7-methoxy-2,3-dihydro-1H-indol-1-yl)-2-oxo-acetamide;
or pharmaceutically acceptable salts thereof.

21. A pharmaceutical composition comprising a compound according to claim 1 in a therapeutically effective amount together with one or more pharmaceutically acceptable carriers or diluents.

22. A method of treating depression comprising administration of a therapeutically effective amount of a compound according to claim 1 to a patient in need thereof.

23. A pharmaceutical composition comprising a compound according to claim 20 in a therapeutically effective amount together with one or more pharmaceutically acceptable carriers or diluents.

24. A method of treating depression comprising administration of a therapeutically effective amount of a compound according to claim 20 to a patient in need thereof.

\* \* \* \* \*